United States Patent [19]
Tyler et al.

[11] Patent Number: 5,409,911
[45] Date of Patent: Apr. 25, 1995

[54] PROSTAGLANDIN ANALOG FOR TREATING OSTEOPOROSIS

[75] Inventors: Peter C. Tyler, Wellington, New Zealand; Robert N. Young, Senneville, Canada; Gideon A. Rodan, Bryn Mawr, Pa.

[73] Assignee: Merck & Co., Inc., Rahway, N.J.

[21] Appl. No.: 944,149

[22] Filed: Sep. 11, 1992

[51] Int. Cl.$^6$ .................... C07F 9/38; A61K 31/66
[52] U.S. Cl. ..................... 514/91; 514/104; 548/413; 560/17; 560/22; 560/160; 562/13
[58] Field of Search ........... 562/13; 560/17, 22, 560/160; 548/413; 514/91, 104

[56] References Cited

U.S. PATENT DOCUMENTS

| | | | |
|---|---|---|---|
| 3,927,197 | 12/1975 | Monkhouse | 560/121 |
| 3,975,404 | 8/1976 | Lincoln | 549/311 |
| 4,018,892 | 4/1977 | Walsh | 560/121 |
| 4,097,601 | 6/1978 | Schaff | 560/121 |
| 4,171,331 | 10/1979 | Biddlecom et al. | 560/121 |
| 4,621,100 | 11/1986 | Lund et al. | 560/121 |
| 4,761,406 | 8/1988 | Flora et al. | 560/121 |
| 4,921,697 | 5/1990 | Peterlik et al. | 560/121 |
| 5,071,655 | 12/1991 | Baylink | 560/121 |
| 5,118,667 | 6/1992 | Adams et al. | 560/121 |

FOREIGN PATENT DOCUMENTS

| | | |
|---|---|---|
| 0179277 | 4/1986 | European Pat. Off. . |
| 0341961 | 11/1989 | European Pat. Off. . |
| 0381296 | 8/1990 | European Pat. Off. . |
| 0496520 | 7/1992 | European Pat. Off. . |
| 2-104593 | 4/1990 | Japan . |
| 2-138118 | 5/1990 | Japan . |

OTHER PUBLICATIONS

Klenner et al. "Anticancer-agent-linked phosphonates with antisteolytic and anti plastic properties: a promising perspective in the treatment of bone-related malignancies?" J. Cancer Res. Clin. Oncol. 116:341-350 (1990).

Frost et al. "Treatment of Osteoporosis by Manipulation of Coherent Bone Cell Populations" Clinical Orthopedics and Related Research, 143, 227 (1979).

Harvey and Bennet "Prostaglandins in Bone Resorption" CRC Press, p. 37 (1988).

Rodan, G. "Cellular Approaches to Therapy for the Prevention and Treatment of Osteoporosis" J. Cell Biochem. Suppl. 0 (15, Part F), 160 (1991).

Ueno et al., "The Effects of Prostaglandin $E_2$ in Rapidly Growing Rats" Bone, 6, 79-86 (1985).

Jee et al., "Long-term anabolic effects of prostaglandin-$E_2$ on tibial diaphyseal bone in male rats:" Bone and Mineral, 15, 33-55 (1991).

Jee et al., "The Effects of Prostaglandin $E_2$ in Growing Rats: Increased Metaphyseal Hard Tissue and Cortico-Endosteal Bone Formation" Calf. tissue Int 37:148-157 (1985).

Raisz et al. "Hormonal Control of Skeletal Growth" Ann. Rev. Physiol. 43:225 (1981).

*Primary Examiner*—Robert Gerstl
*Attorney, Agent, or Firm*—Joanne M. Giesser; Melvin Winokur; Paul D. Matukaitis

[57] ABSTRACT

This invention relates to a prostaglandin-bisphosphonate compound of the formula:

and its pharmaceutically acceptable salts. The claimed compounds are effective as delivery agents of prostaglandins to treat osteoporosis and related bone diseases. The claimed compounds also simultaneously deliver a bisphosphonate which inhibits bone resorption and delivers prostaglandins which increase bone formation in vivo.

13 Claims, 2 Drawing Sheets

PROSTAGLANDIN ANALOG FOR TREATING OSTEOPOROSIS

BACKGROUND OF THE INVENTION

The compounds of the present invention are analogues of the natural prostaglandin $PGE_2$, $PGE_1$ and $PGF_2$alpha useful in the treatment of osteoporosis. Prostaglandins are alicyclic compounds related to the basic compound prostanoic acid. The carbon atoms of the basic prostaglandin are numbered sequentially from the carboxylic carbon atom through the cyclopentyl ring to the terminal carbon atom on the adjacent side chain. Normally, the adjacent side chains are in the trans orientation. $PGE_2$ has the following structure:

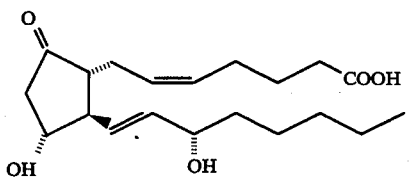

The presence of an oxo group at C-9 of the cyclopentyl moiety is indicative of a prostaglandin within the E class while $PGE_2$ contains a trans unsaturated double bond at the $C_{13}$-$C_{14}$ and a cis double bond at the $C_5$-$C_6$ position. U.S. Pat. No. 4,171,331 teaches 1 and 2 substituted analogues of certain prostaglandins. Disclosed are trans 1 and 2 di(loweralkyl)phosphono; 1 and 2 chloro, bromo, and iodo; 1 and 2-thio; and 1 and 2 amino analogues of $PGE_1$. U.S. Pat. No. 3,927,197 discloses the formation of various acid derivatives of prostaglandins such as amides, carboxylate-amine salts, and the 2-decarboxy-2-(2,3,4,5-tetryol-1-yl) derivative.

Osteoporosis is the most common form of metabolic bone disease and is commonly observed in post-memopausal women but also occurs in elderly males and females or in young individuals. Commonly, the disease is characterized by fractures of the wrist and spine, while femoral fractures are the dominant feature of senile osteoporosis. The physical causitive factor which creates susceptibility to fracturing is the gradual loss of bone or bone minerals such as calcium. Apparently, the normal balance of bone resorption activity by the osteoclasts (bone dissolving or resorbing cells) and bone formation activity by the osteoblasts (bone forming cells) is disrupted by development of the disease so that the cavities created by the osteoclasts are not refilled by the osteoblasts. A number of pharmaceutical compounds are known in the art which hinder the activity of osteoclasts so that bone loss is diminished. For example, bisphosphonates as a class are useful in inhibiting bone loss and are therefore important in treating diseases associated with bone loss, including osteoporosis. A more difficult treatment regime or area has been the effective acceleration or stimulation of bone formation to maintain bone growth or strengthen weakened bones.

It is clear, however, that the activity of osteoblasts and osteoclasts is coordinated and regulated by a complex mechanism and is affected by a variety of hormones and prostaglandins. See Raisz et al., *Ann. Rev. Physiol.*, 43:225 (1981); U.S. Pat. No. 4,921,697 which teaches that inhibition of prostaglandin production by IFN-gamma is an effective treatment for osteoporosis and other bone-resorption diseases since prostaglandins have been implicated in bone loss or resorption. The literature also suggests that pro staglandins may also play an important role in bone formation. See W. Harvey and A. Bennett, "Prostaglandins in Bone Resorption" CRC Press, pp. 37 (1988). Osteoblasts are responsible for carrying out the bone formation process. It has been established that bone formation in vivo in animals is stimulated by systemic injection of $PGE_2$. See Rodan G. *J. Cell Biochem. Suppl.* 0 (15 Part F), 160 (1991).

The effects of prostaglandins administered alone has been disclosed in the art. Ueno et al., Bone, 6, 79–86, (1985) administered $PGE_2$ to rapidly growing rats at dosages of 1, 3 and 6 mg of $PGE_2$/Kg/day. The results showed an increase in hard tissue mass in the secondary spongiosa of the proximal tibial metaphysis and an increase in the number of trabeculae. Jee et al., Bone and Mineral, 15, 33–55 (1991), disclosed that subcutaneous injections of $PGE_2$ over 60, 120, and 180 days produced an increased tibial diaphyseal bone mass and elevated bone activity. The authors reported that the anabolic effects of $PGE_2$ increases periosteal and corticoendosteal bone mass and sustains the transient increase in bone mass with daily administration of $PGE_2$. It is known that very little control is possible over the duration and the concentration at which PGs reach the bone cells. It is also known that systemic injection or infusion of PGs is an alternative with significant drawbacks since the lungs efficiently remove PGs from circulation. See W. Harvey and A. Bennett, "Prostaglandins in Bone Resorption" CRC Press, pp. 37 (1988).

It is also known that toxicity of prostaglandins due to systemic distribution of the administered drug reduces or diminishes the pharmaceutical utility of these compounds. Delivery of high doses of prostaglandins which would be necessary because of the short half life of these compounds may cause unwanted side effects. Ueno et al reported that when $PGE_2$ was administered systemically through subcutaneous injections to rats, diarrhea and flushing of the extremities along with weight loss occurred at doses of 3 mg/Kg/day or higher. In addition, significant decreases in serum phosphate levels of 1 mg of $PGE_2$ were noted. Jee et al reported that long term administration of $PGE_2$ administered via subcutaneous injection resulted in soft tissue weight increases in adrenal glands, liver, kidneys, and lungs. U.S. Pat. No. 4,621,100 discloses side effects after oral dosing with $PGE_2$ including loose stools, diarrhea, vomiting, infected sclerae, and increased serum alkaline phosphatase levels.

Frost et al. in "Treatment of Osteoporosis by Manipulation of Coherent Bone Cell Populations", *Clinical Orthopedics and Related Research*, 143, 227 (1979) discloses a theoretical model that suggests it should be possible to synchronize the activity and metabolism of bone cells by administering bone cell activating agents first and then administering a bone resorption inhibiting agent. This proposed model assumes that bone formation inhibition does not take place, because no bone resorption inhibiting agent is administered during the bone formation phase of the bone remodeling unit. EPO App. No. 0 381 296 teaches the use of a kit wherein a bone activating period or treatment regime is followed by a bone resorption inhibiting regime. Examples of bone activating compounds cited in this reference include parathyroid hormone (PTH), inorganic phosphate, growth hormone, fluoride, thyroid hormone (e.g. thyroxin), certain vitamin D metabolites and prostaglandins (PGE$_2$ in a dose regime of 10 mg/kg per day). See also U.S. Pat. No. 5,118,667. Examples of bone resorption inhibiting polyphosphonates include ethane-1-hydroxy 1,1-diphosphonic acid, methane diphosphonic acid, pentane-1-hydroxy-1,1-diphosphonic acid, methane dichloro dipho sphonic acid, methane hydroxy dipho sphonic acid, ethane-1-amino- 1,1-diphosphonic acid, propane-N,N-dimethyl-3-amino -1-hydroxy-1,1-diphosphonic acid, propane-3-3-dimethyl-3-amino-1-hydroxy-1,1-diphosphonic acid, phenyl amino methane diphosphonic acid, N,N-dimethylamino methane diphosphonic acid, N(2-hydroxyethyl) amino methane diphosphonic acid, butane-4-amino-1-hydroxy-1,1-diphosphonic acid (administered after PGE$_2$ at a dosage per day of 0.005 mg P/kg), pentane-5-amino-1-hydroxy-1,1-diphosphonic acid, and hexane-6-amino-1-hydroxy-1,1-diphosphonic acid. Combinations of a methylene bisphosphonate coupled to a medicinal compound such as a Non-Steroidal Anti-Inflammatory Agent (NS AID) have been disclosed. See Japanese Patent Publication No. H2-104593.

The present invention, on the other hand, provides simultaneous delivery of a bone activating agent such as a prostaglandin that is chemically coupled to a bone resorption inhibiting compound which selectively delivers the bone activating agent to the target area. Upon gradual hydrolysis of the novel compound, the hydrolyzed products are able to provide bone resorption inhibiting activity (via the bisphosphonates) and bone growth or stimulating activity (via PGE$_2$). The present invention also enables more effective delivery of PGE$_2$ to the target region and therefore overcomes the serious side effect disadvantages associated with administration of larger quantities of PGE$_2$ alone. In addition, PGE$_2$ administered systemically has a short half-life. The present invention overcomes the disadvantages prevalent in the background art and at the same time provides a compound that promotes bone growth and deters bone resorption to provide a treatment for osteoporosis and related disorders of calcium metabolism.

SUMMARY OF THE INVENTION

The claimed invention's primary objective is to use compounds within the scope of the invention as chemical delivery agents of prostaglandins. This invention claims a novel chemical method for simultaneously delivering a bone formation enhancer such as a prostaglandin and a bone resorption inhibitor such as an amino bisphosphonate. The invention is a prostaglandin-bisphosphonate compound which when administered systemically has high affinity for bone cells. The compounds of the invention are then hydrolyzed to form a bisphosphonate and a prostaglandin. The invention is useful in the prevention and treatment of osteoporosis and has the distinct advantage that lower doses of prostaglandins may be administered to a mammal or patient in need thereof since the prostaglandin is delivered to the site of action before it is metabolized. This method also avoids the undesirable side affects associated with higher doses of prostaglandins. The invention is also directed to a compound of the following formula:

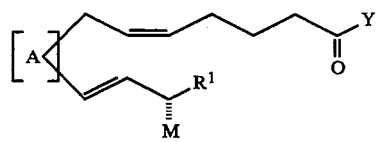

and the pharmaceutically acceptable salts thereof wherein:

[A]

is a dioxygenated cyclopentane moiety of the formula:

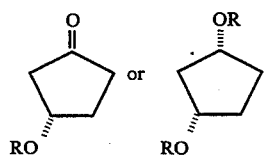

wherein
R is:
H,
THP, or
Si(CH$_3$)$_2$tBu;
R$^1$ is:
H, or
C$_{1-10}$ alkyl;
M is:
OH,
OC$_{1-6}$ alkyl,

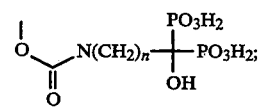

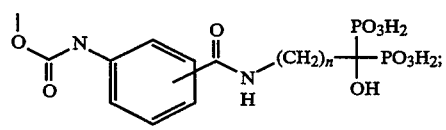

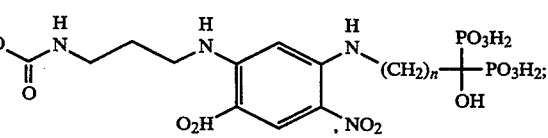

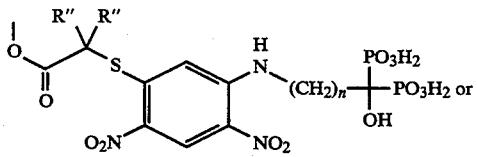

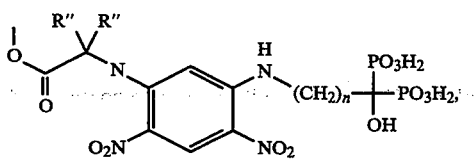

wherein R" is H, C$_{1-10}$ alkyl, aryl, or benzyl;

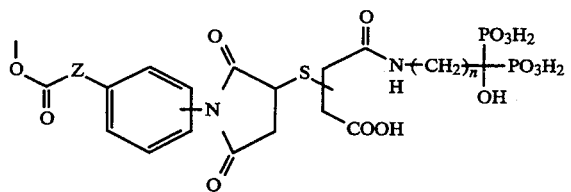

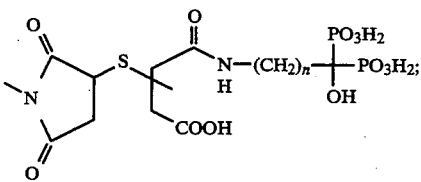

wherein Z is NH, C(R¹)₂, or absent;

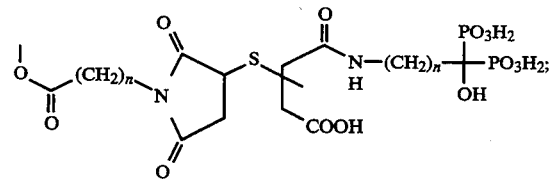

Y is:

OR' wherein R' is $C_{1-6}$ alkyl; or

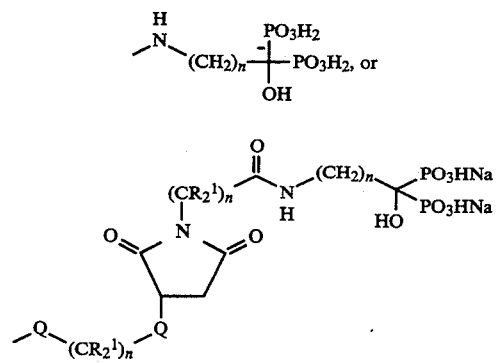

wherein Q is NR¹, O, or S,

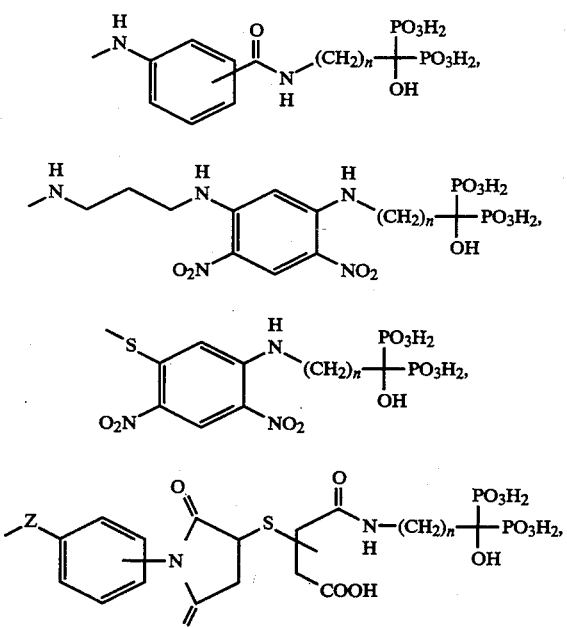

wherein Z is HN, C(R¹)₂ or absent, or and n is an integer from 1-10.

This invention is also directed to a method of treating or preventing osteoporosis by administering a pharmaceutically effective amount of the compound according to claim 1. It is directed to a method of increasing the bone fracture healing rate in a mammal exhibiting a bone fracture by systemically administering a pharmaceutically effective amount of the compound according to claim 1 and to method for enhancing the rate of successful bone grafts comprising administering to a mammal in need thereof a pharmaceutically effective amount of the compound according to claim 1. This invention is advantageously directed to a method of delivering a prostaglandin according to claim 1 to a mammalian organism in need of treatment thereof via a bisphosphonate delivery agent wherein the prostaglandin enhances the rate of bone formation and is thus effective in treating osteoporosis, bone fractures, and effective in enhancing the rate of successful bone grafts.

DETAILED DESCRIPTION OF THE INVENTION

Figure 1:
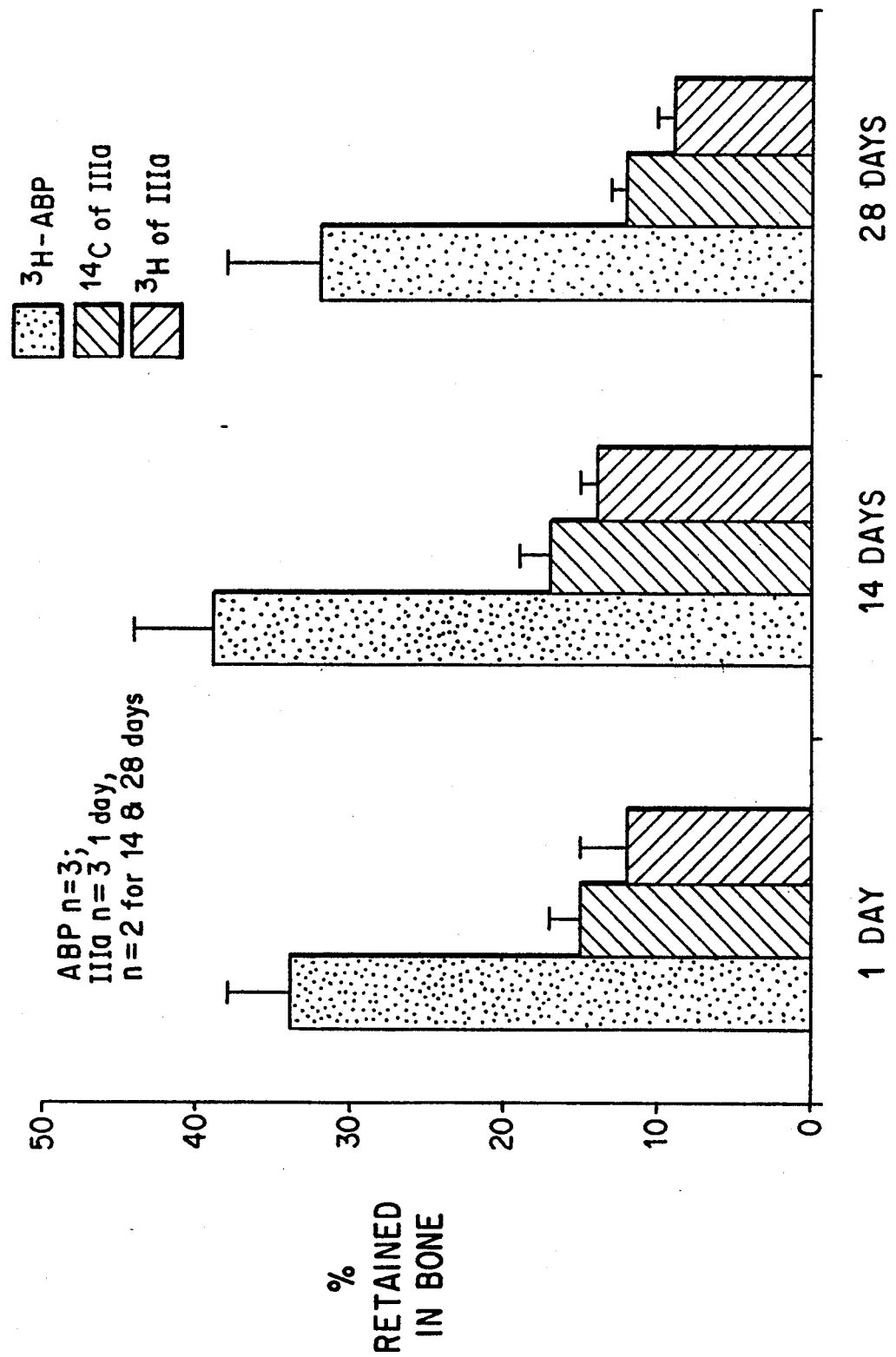
FIG. 1 shows uptake of the $^{14}C$— and 3H— moieties of compound IIIa by rat tibiae and femora after a single dose of the compound was administered intravaneously (i.v.). Animals were sacrificed at 24 hours, 14 and 28 days and the long bones were incinerated and the radioactivity measured. This Figure shows that there was approximately 15% total uptake of IIIa compared to approximately 34% of an equimolar dose of $^3H$-alendronate.

This invention comprises a compound that is effective as a chemical delivery agent and a compound which is useful in the treatment and prevention of osteoporosis and calcium metabolism disorders. The compound of the invention may also have dual activity as a bone growth promoter and as a bone resorption inhibitor. Prostaglandins of the PGE₂, PGE₁ and PGF₂a class or other suitable prostaglandin with a carboxylic acid moiety at the 1 position and a hydroxyl group at the 15 position of the PG moiety may be reacted with an amino bisphosphonate such as ABP or its salts to form the compounds claimed in the instant invention. Any known bisphosphonate which has an amine fuctionality capable of coupling to a prostaglandin and which targets in vivo to bone may be used in this invention as a chemical delivery agent whether or not that particular bisphosphonate has bone resorption inhibiting activity.

The following scheme describes a synthesis of a bisphosphonate-prostaglandin compound:

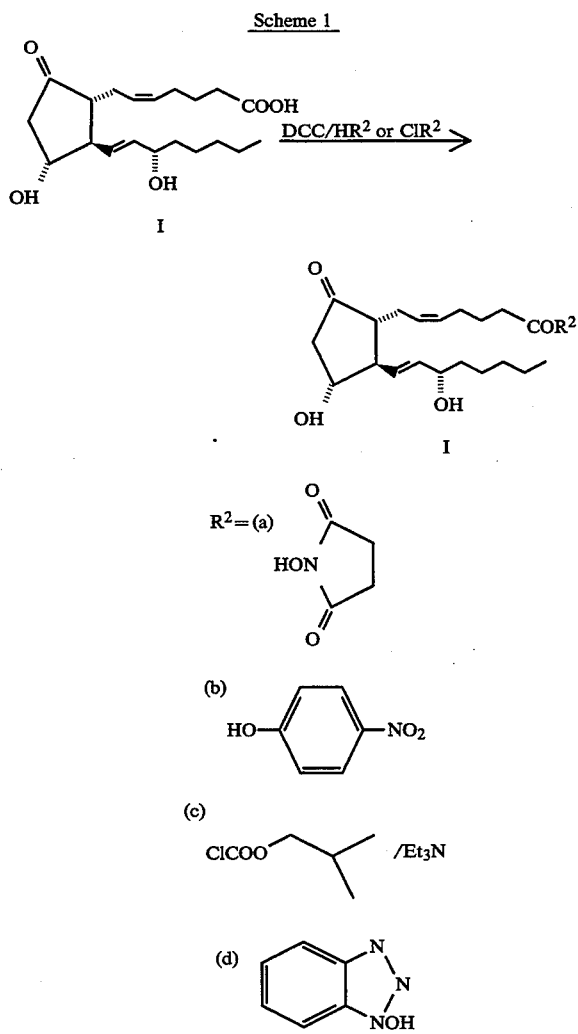

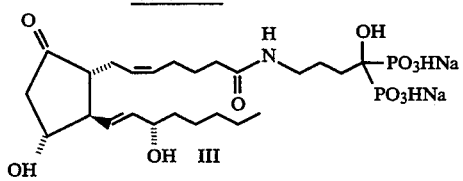

1,3-Dicyclohexylcarbodiimide is added to a stirred solution of PGE$_2$ (I) or other suitable prostaglandin and N-hyroxysuccinimide in dry acetonitrile and stirred at room temperature (25° C.) until thin layer chromatography or other suitable analytical method such as HPLC indicates that the reaction is complete. The solvent is removed under an inert atmosphere (nitrogen) and the residue is dissolved in methylene chloride and applied to a small column of silica gel in a pasteur pipette. The pipette is then eluted with ethyl acetate to afford the hydroxysuccinimide ester (IIa) and a small quantity of dicyclohexylurea. A solution of this ester in 1,4-dioxane is added to a stirred solution of a suitable bisphosphonate such as ABP in water and 1.0 molar (M) aqueous NaOH. After 10 minutes or so the pH of the reaction mixture is adjusted to approximately 9 with 1.0M aqueous NaOH, and then 1 hr later the pH is adjusted to 7 with 0.1M aqueous HCl. The solution is filtered and the filtrate is concentrated to dryness. The residue is then dissolved in water and applied to a Varian Bond Elute C$_{18}$ pak which is eluted with water. When the product begins to elute, the solvent system on the C$_{18}$ column is changed to acetonitrile/water (50:50). Evaporation of fractions containing the product will afford the target amide (III).

The prostaglandins used in the above scheme can be chosen from the PGE$_2$ class or from the PGF$_a$ class or from any prostaglandin or prostaglandin analog which has known bone growth enhancement activity. A compound of the general formula depicted below is reacted with DCC to form the activated ester V which is then reacted with an aminoalkylbisphosphonate to form the coupled amide product.

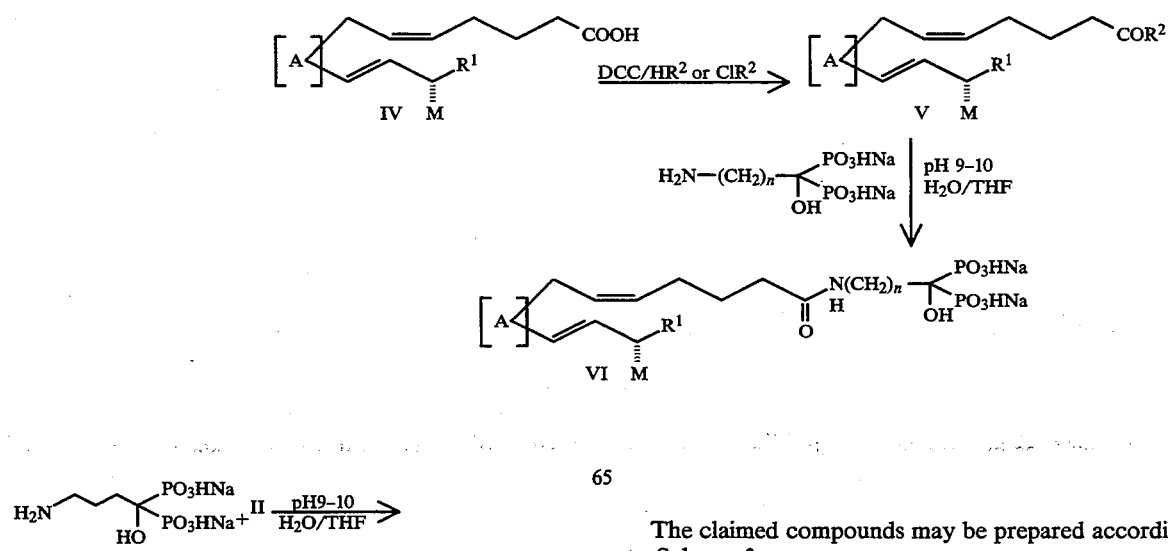

The claimed compounds may be prepared according to Scheme 3:

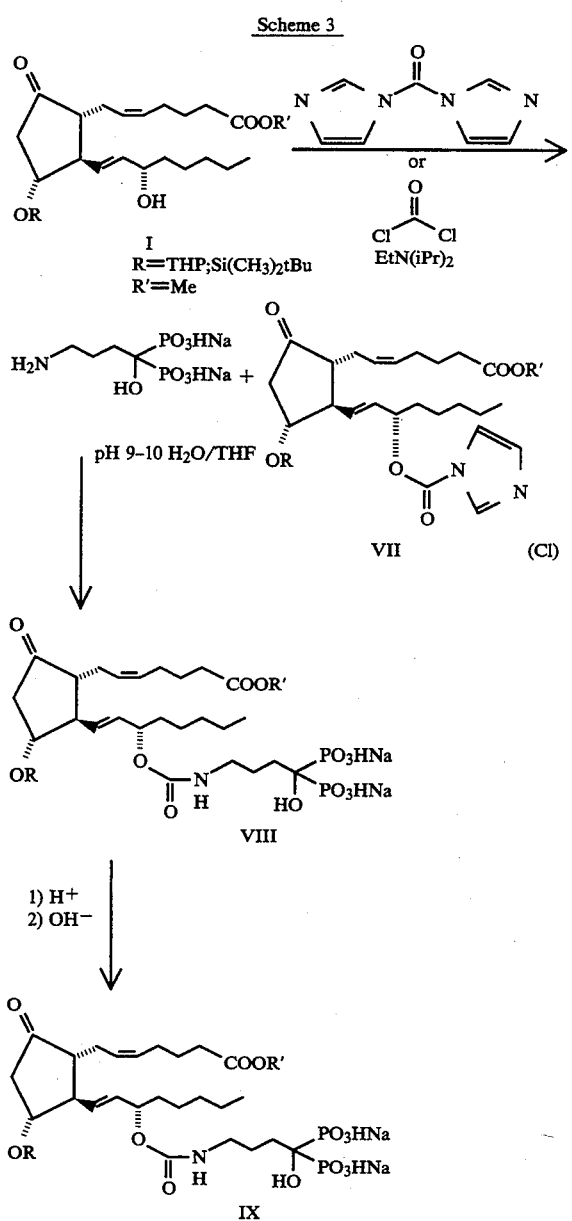

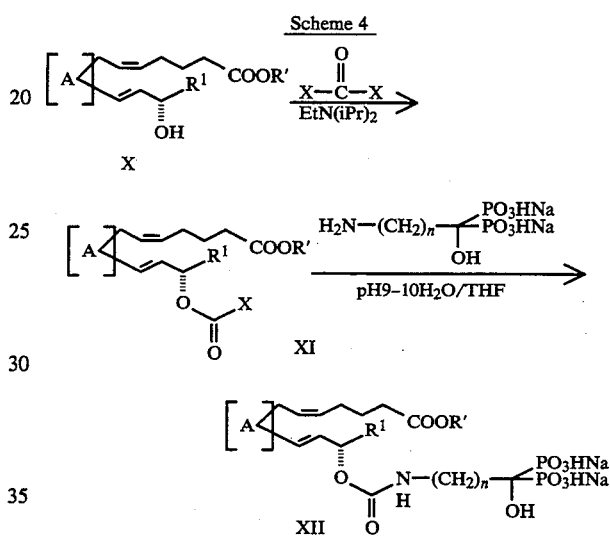

The silyl protected PGE$_2$ is prepared and reacted with an activated carbonyl compound at the C$^{15}$ hydroxy to form the activated ester. This reactant is then treated with a bisphosphonate such as ABP disodium salt to form a prostaglandin-bisphosphonate ester compound that can deliver the prostaglandin to the bone cells and is more labile to enzymatic hydrolysis.

The prostaglandins used in the above scheme to produce the amido ester derivative may be chosen from the PGE$_2$ or PGFa class. A compound of the general formula depicted below is reacted with oxodiimidazole or oxalyl chloride or reactant of the general formula CO(X)$_2$ to form the activated ester which is then reacted with an aminoalkylbisphosphonate salt to form the coupled amido ester product.

Compounds of the instant invention may also be prepared according to the following scheme:

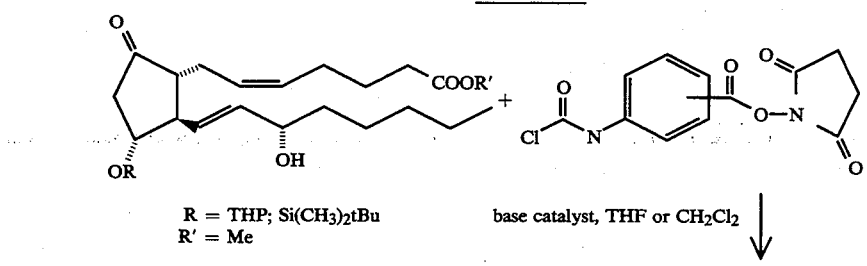

Scheme 5

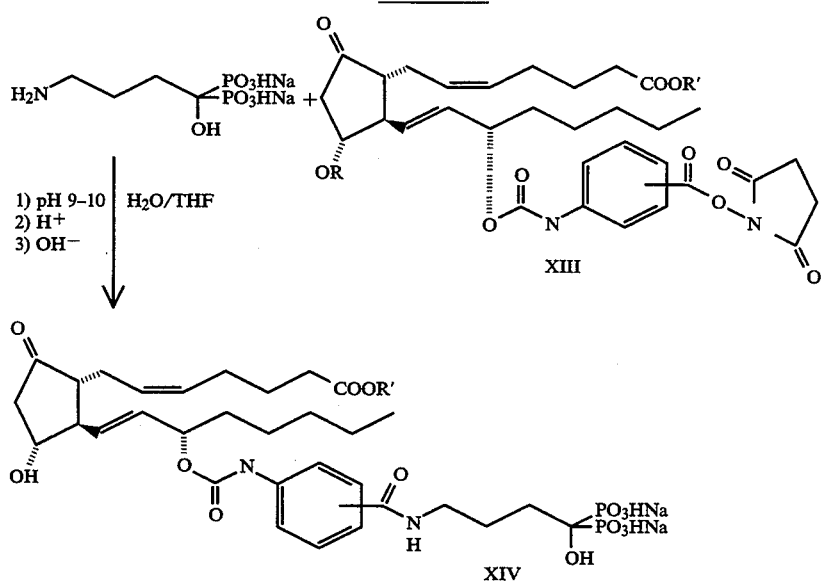

Protected PGE$_2$ is reacted with an amide chloride or a bifunctional reagent such as 2- (or 3-, or 4-) succinamido-N-oxycarbonylphenylamino carbonyl chloride using a base catalyst in THF or in methlene chloride to form the activated PGE$_2$ analog which is further reacted with a bisphosphonate such as the disodium salt of ABP in aqueous THF at pH 9–10. The resultant bisphosphonate-PG compound is hydrolyzed to remove the protecting groups on the cyclopentane moiety to give compound XIV. The prostaglandins used in the above scheme can be chosen from the PGE$_2$ or PGF$_2$a class. A compound of the general formula depicted below is reacted with a diactivated ester species to form a reactive intermediate which is reacted with a bisphosphonate salt to form the coupled product.

Scheme 6

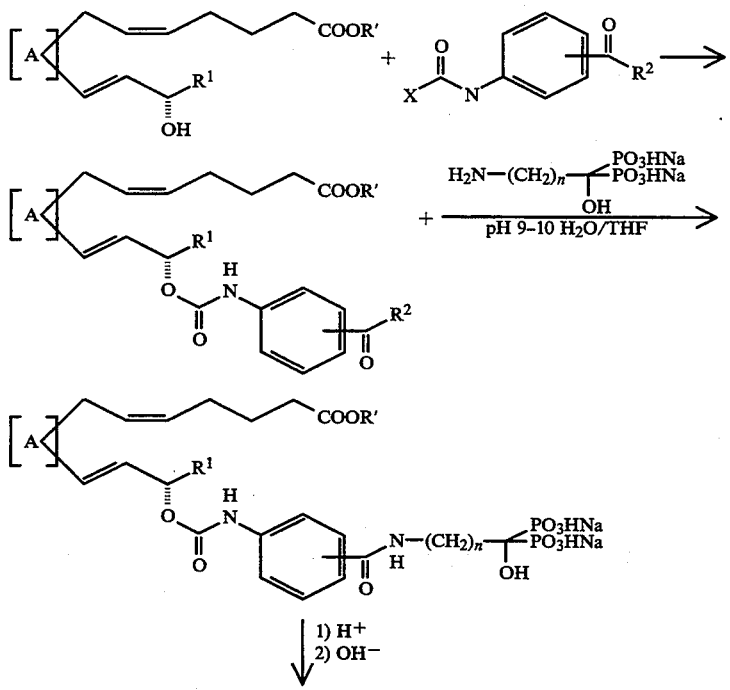

Scheme 6
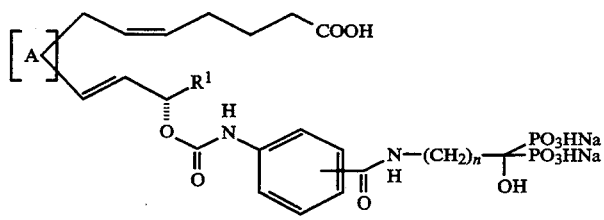
Alternatively, the compounds of the instant invention may be prepared according to the following scheme:
Scheme 7
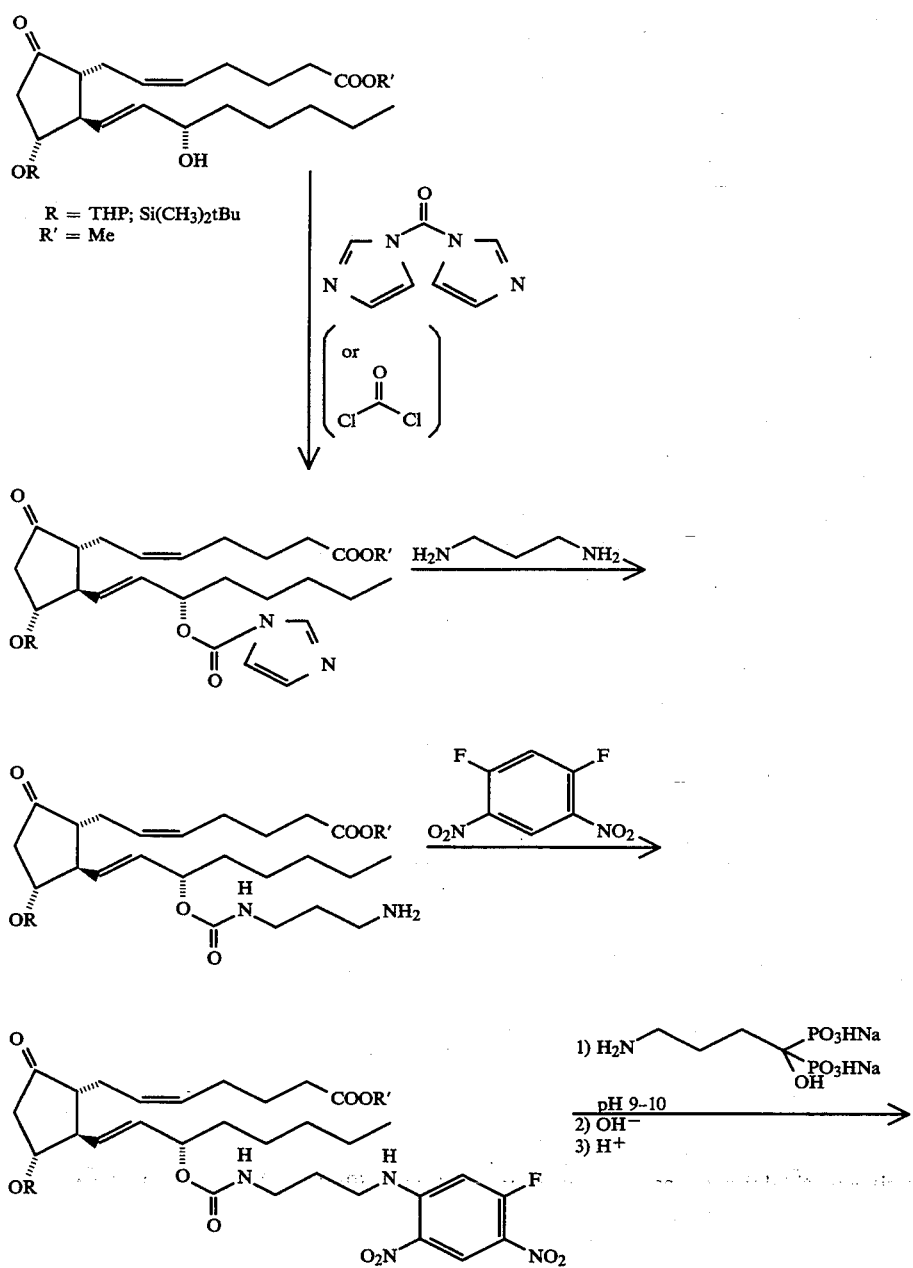

Scheme 7

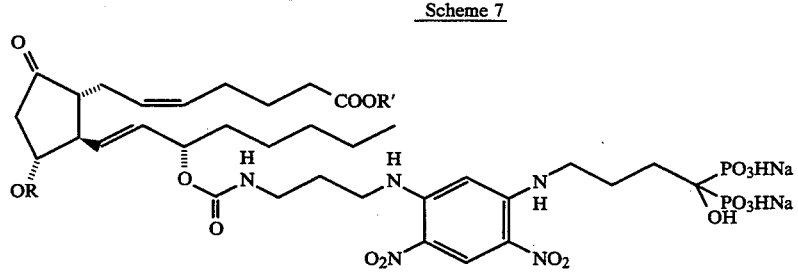

The protected prostaglandin is reacted with carbonyl-diimidazole or oxalyl chloride to form the 15 hydroxy ester which is further reacted with 1,3-diaminopropane and 1,3-difloro-4,6-dinitrobenzene to form the dinitrophenyl-amino amide-PG analog shown in Scheme 7. The disodium salt of ABP acts as a nucleophile and displaces fluorine to form the PG-bisphosphonate molecule which is then hydrolyzed to remove the remaining protecting groups. Scheme 8 below describes a general synthesis wherein the particular prostaglandin used may be from the $PGE_2$, $PGE_1$ or $PGF_{2a}$ series.

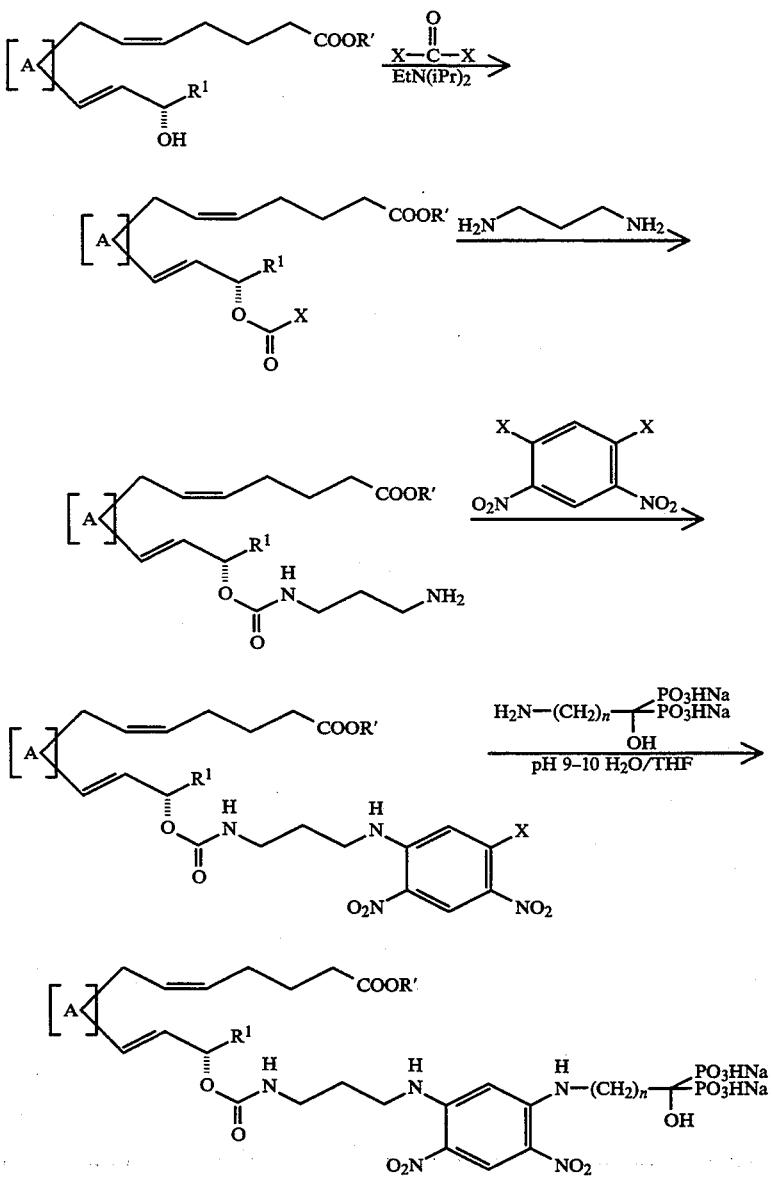

Scheme 9 depicts another method of producing the claimed compounds.

Scheme 9

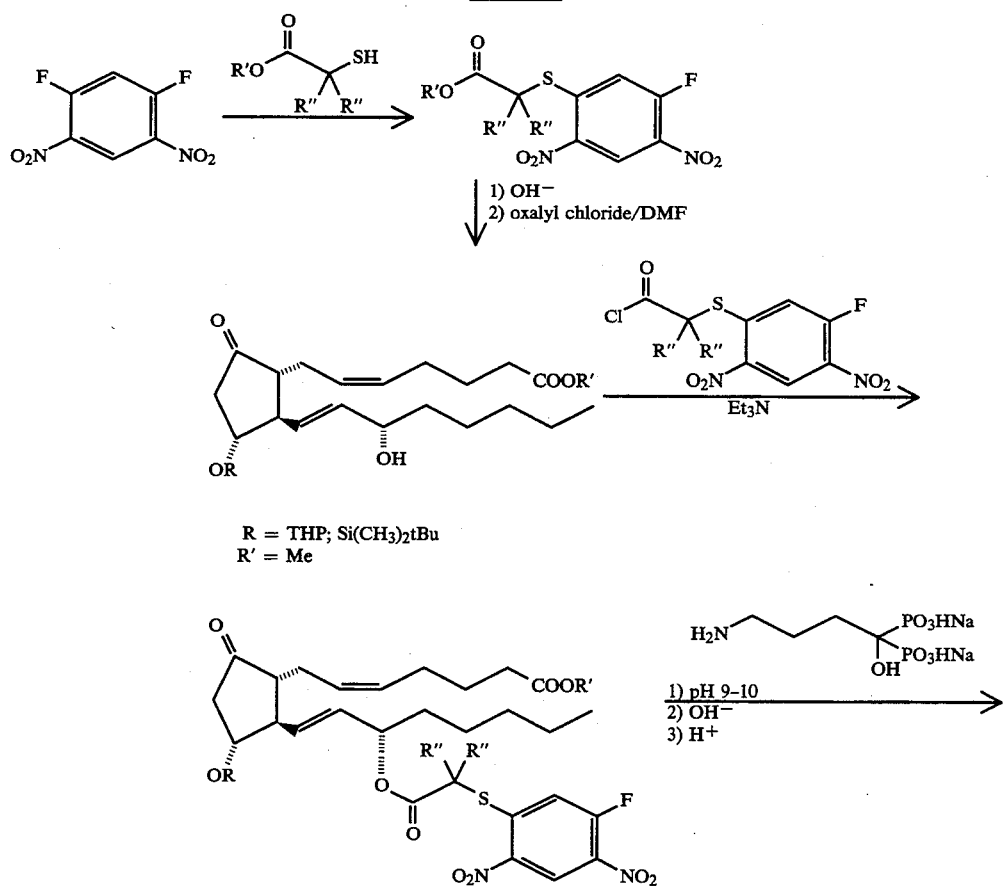

R = THP; Si(CH₃)₂tBu
R' = Me

R" is H, C₁₋₁₀ alkyl, aryl or benzyl.

The diflouro,dinitro benzene is reacted with a mercaptyl ester to form the thioaromatic species which is further reacted with base and oxalyl chloride to form the activated aromatic species. This is reacted with protected PGE₂ to form the thioaromatic-PGE₂ compound which is reacted with a bisphosphonate such as ABP disodium salt and then hydrolyzed to give the PGE₂-bisphosphonate compound which contains the aromatic linking moiety. A similar reaction scheme may also be performed wherein an NH moiety replaces the thio group to give a compound of the formula:

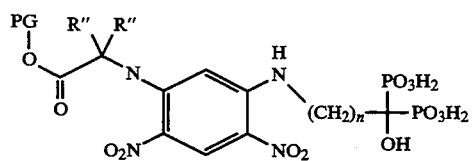

This reaction may also be performed on members of the PGE₂, PGE₁ or PGF₂ₐ class as shown below:

Scheme 10
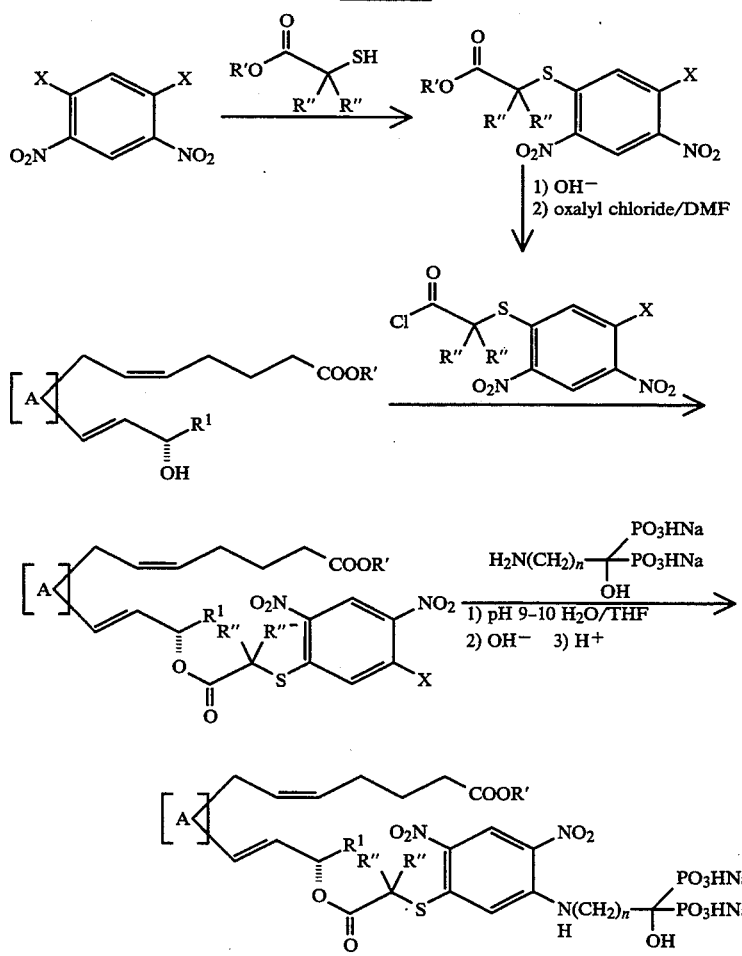
wherein S may be replaced by NH or NR.
Scheme 11
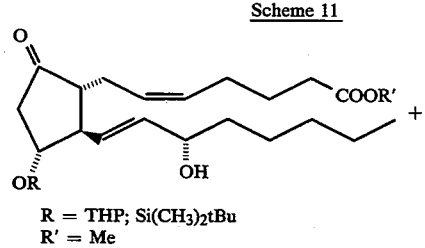
R = THP; Si(CH$_3$)$_2$tBu
R' = Me
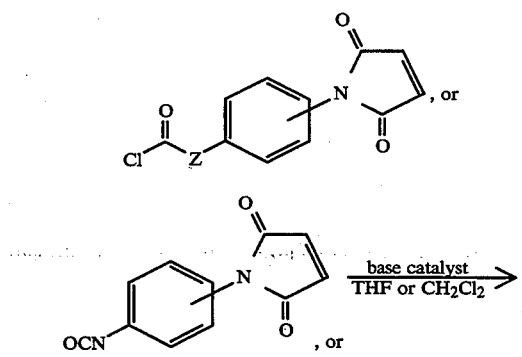
-continued
Scheme 11
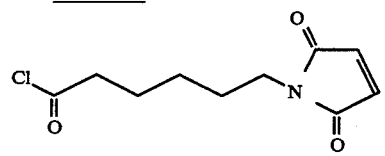
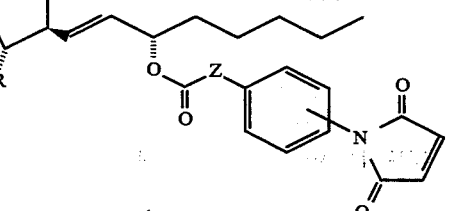
Z = NH or C(R$^1$)$_2$ or bond
(2a)

-continued
Scheme 11
The claimed compounds may be prepared as described in Scheme 11 and may be further reacted as shown in Scheme 12.
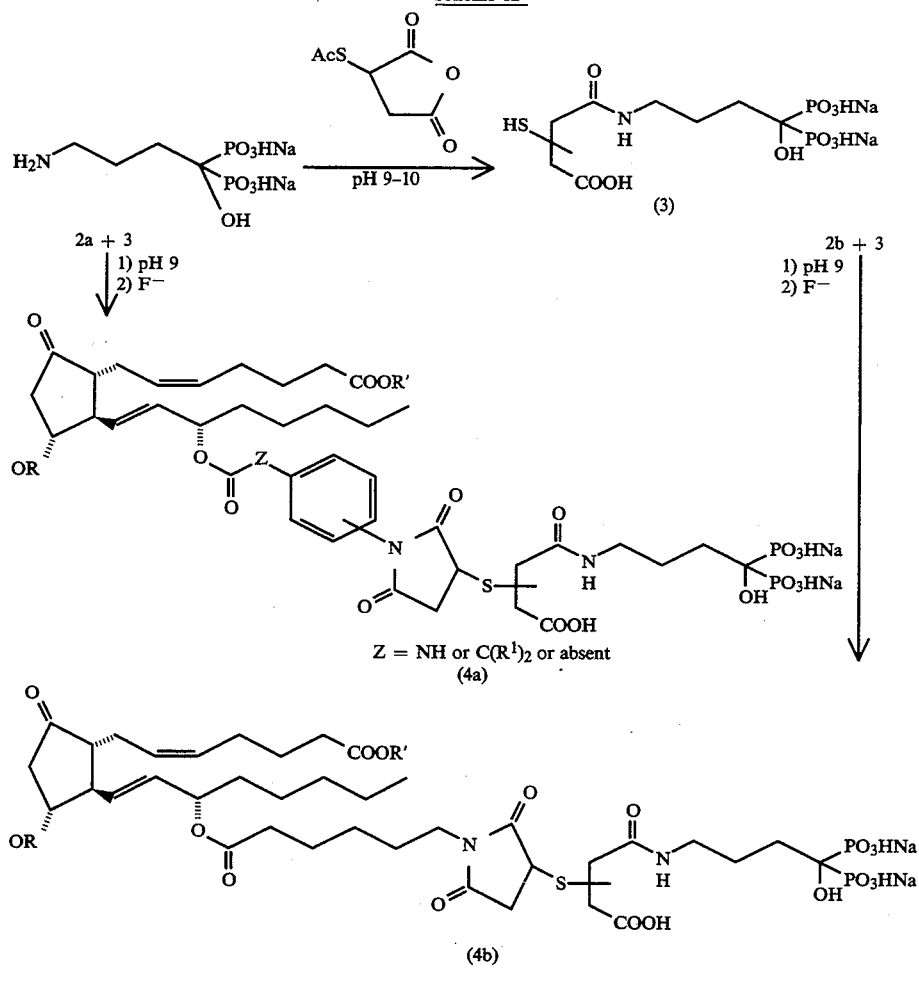
Scheme 13 exemplifies production of the claimed compounds.
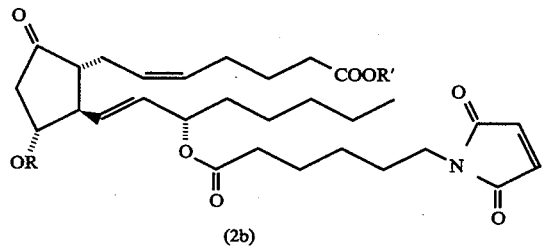
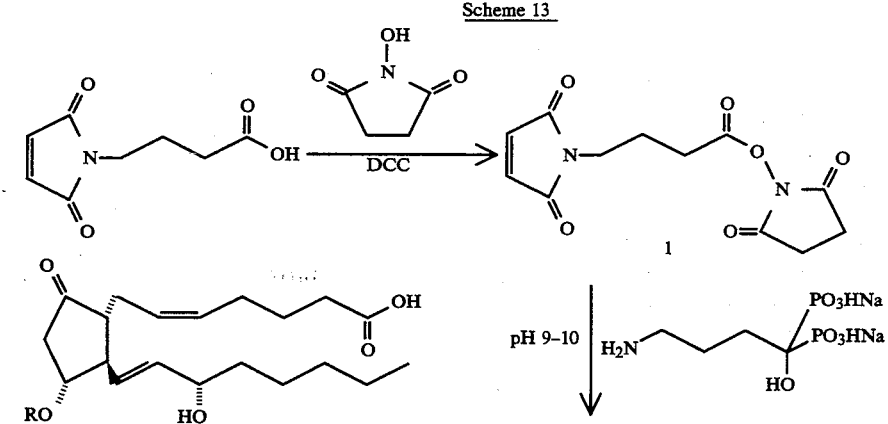

Scheme 13

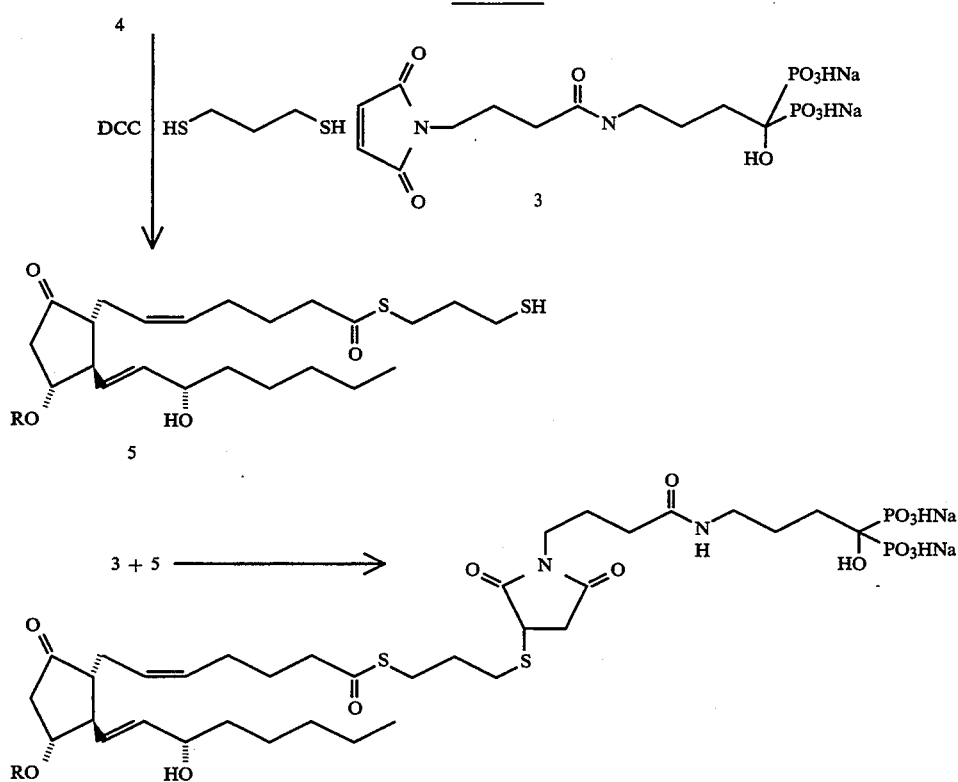

As shown above, DCC is added to a solution of N-(4-carboxybutyl) maleimide in a suitable solvent such as dichloromethane that contains N-hydroxysuccinimide. The reaction is allowed to proceed for several hours and is then purified to afford the activated ester 1. A solution of this ester is then added to a stirred solution of a suitable biphosphonate such as but not limited to ABP in water and sodium hydroxide. The reaction is allowed to proceed for several minutes and then the pH is adjusted to 7 and then the batch is lyophilized. The resulting powder is then purified via a suitable means such as HPLC and the resultant purified powder is again lyophilized. Compound 3 or other suitable aminobisphosphonate maleimide derivative is produced. In a separate process, a suitable prostaglandin derivative, such as PGE$_2$ or others as disclosed in the instant invention, is reacted with DCC and a dithiol compound (such as 1,3-propanedithiol) or other suitable dinucleophilic agent such as 3-thio-1-propanol (protected as necessary) to form a compound such as 5. The suitable prostaglandin analog such as 5 is then reacted with compound 3 or other aminobisphosphonate maleimide to form a final product such as that depicted in Scheme 13. It is understood that other derivatized prostaglandins which have an activated ester group at the C-1 position may be reacted with aminoalcohols, thiolalcohols, or dithiols to form compounds analogous to 5. For example, Scheme 14 shows the reaction of an analog of 5 wherein Q is O, NR$^1$, or S and the carbon chain may be a substituted or unsubstitued chain of 1-10 carbon atoms (n=1-10) with the aminobisphosphonate maleimide shown above to form the depicted ester, amide or thioester derivative. This compound may be used as an effective delivery agent of a prostaglandin.

Scheme 14

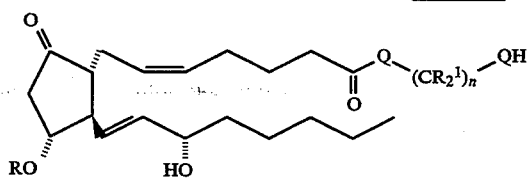

Scheme 14 -continued

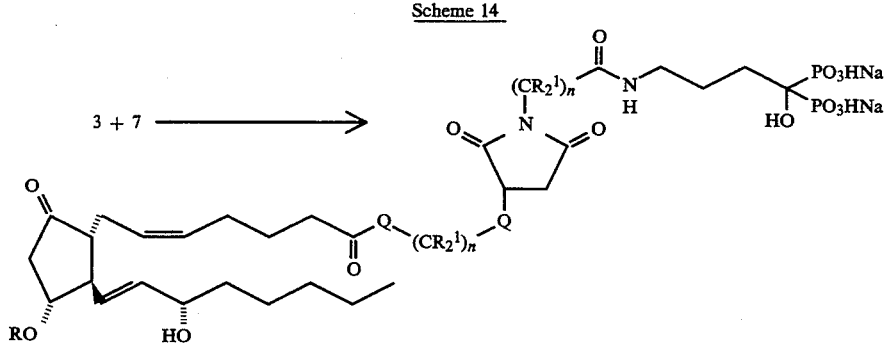

The claimed compounds may be used in treating a variety of calcium metabolism disorders including:
(1) A method of treating or preventing osteoporosis by administering a pharmaceutically effective amount of compounds within the scope of the present invention.
(2) A method of increasing the bone fracture healing rate in a mammal exhibiting a bone fracture by systemically administering a pharmaceutically effective amount of compounds within the scope of the present invention.
(3) A method for enhancing the rate of successful bone grafts comprising administering to a mammal in need thereof a pharmaceutically effective amount compounds within the scope of the present invention.
(4) A method of treating periodontal disease or alveolar bone loss by administering a pharmaceutically effective amount of compounds within the scope of the present invention.

The bisphosphonates which may be used in the present invention include any aminoalkyl bisphosphonate such as alendronate, pamidronate (3-amino-1-hydroxypropylidene) bisphosphonic acid disodium salt, pamidronic acid, riserdronate (1-hydroxy-2-(3-pyridinyl)ethylidene)bisphosphonate, YM 175 ((cycloheptylamino) methylene-bisphosphonic acid, piridronate, aminohexanebisphosphonate, tiludronate, BM-210955, CGP-42446, and EB-1053.

The novel method of delivering prostaglandins via the claimed compounds disclosed and claimed in the instant invention to the site at which bone growth stimulation is desired requires, in order to enhance bone formation, daily delivery of about 0.0001 to about 1 mg of prostaglandin. The preferred range to achieve increased bone volume is between 0.1 μg and 0.3 μg per day of PGE$_2$. Cortical bone mass may also be increased using a PGE$_2$ equivalent dose of 0.3 μg per day. The quantities delivered via the novel method claimed in the instant invention are clearly an improvement over the 3 mg/day necessary to achieve an equivalent bone formation effect when a prostaglandin is administered systemically.

The prostaglandins which may be used in the present invention include but are not limited to PGE$_2$, PGE$_1$, and their analogs and PGF$_{2\alpha}$ and its analogs. The invention also encompasses pharmaceutical compositions containing compounds within the scope of the invention as active ingredients and those fillers or other inactive ingredients which those skilled in the art recognize as important for the safe and effective delivery of the claimed composition to a patient or patients in need thereof.

Protecting groups utilized in the synthesis of compounds within the scope of the present invention include, but are not limited to, THP. Other well known alcohol protecting groups include benzyl halides, MEM, and alkylcarbonylhalides.

The following examples demonstrate both the syntheses of some of the compounds within the scope of the present invention and also demonstrate the specific ability of the claimed compounds to target to bone cells in vitro and in vivo. The examples show that the uptake of $^{14}$C/$^3$H dual labeled compound shown below and claimed in the instant invention to human bone powder in vitro occurs within one minute in fetal bovine serum. About 77% of the $^{14}$C moiety and 53% of the $^3$H moiety of the compound shown below is taken up by the bone powder. Dissociation of the PG moiety from the bisphosphonate from human bone powder in fetal bovine serum occurs at a rate of approximately 5%/day at 37° C. Both radiolabel experiments and radioimmunoassay experiments confirm release of the prostaglandin from the bisphosphonate at the bone cell site.

In vivo experiments also demonstrate that compounds disclosed and claimed in the present invention are delivered to bone. For example, uptake of the labeled compound shown below into rat tibiae and femora after a single dose was administered intravaneously was demonstrated. The animals used in this experiment were sacrificed at 24 hours, 14 and 28 days after the compounds claimed in the instant invention were administered. The radioactivity of the $^{14}$C and $^3$H was measured after incineration of the long bones to determine the percentage of compound retained in the bone. The examples further show that compounds within the scope of the present invention significantly inhibit the production of lysylpyridinolines (LP) over certain time periods. High LP levels are normally associated with the breakdown of bone collagen.

The compounds claimed in the instant invention are therefore useful in the treatment of diseases or conditions in which bone loss or degradation or fracture has occurred. The compounds claimed in the instant invention, as the specification discloses and as the schemes and examples demonstrate, administered in pure form or in a pharmaceutical composition are effective in delivering a bone healing or bone growth enhancing amount of a prostaglandin to a patient or organism in need of such treatment. In addition, the compounds may also be used as bone growth enhancers and bone resorption inhibitors if the particular bisphosphonate used has bone resorption inhibiting activity or if the entire compound prior to hydrolysis has bone resorption inhibiting activity.

The term "pharmaceutically acceptable salts" shall mean nontoxic salts of the compounds of this invention which are generally prepared by reacting the free base with a suitable organic or inorganic acid. Representative salts include the following salts: Acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, glucoheptanate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylbromide, methylnitrate, methylsulfate, mucate, napsylate, nitrate, oleate, oxalate, pamaote, palmitate, pantothenate, phosphate/diphosphate, polygalactouronate, salicylate, stearate, subacetate, succinate, tannate, tartrate, teoclate, tosylate, triethiodide, valerate.

The term "pharmaceutically effective amount" shall mean that amount of a drug or pharmaceutical agent that will elicit the biological or medical response of a tissue, system or animal that is being sought by a physician or veterinarian.

The term "aryl" shall mean a mono- or polycyclic system s composed of 5- and/or 6-membered aromatic tings containing 0, 1, 2, 3, or 4 heteroatoms chosen from N, O or S and either unsubstituted or substituted independently with $R^1$ to $R^{12}$. The term "alkyl" shall mean straight or branched alkane, alkene or alkyne. The term "alkoxy" shall be taken to include an alkyl portion where alkyl is as defined above.

The terms "arylalkyl" and "alkylaryl" shall be taken to include an alkyl portion where alkyl is as defined above and to include an aryl portion where aryl is as defined above. The $C_{0-n}$ or $C_{1-n}$ designation where n may be an integer from 1–10 or 2–10 respectively refers to the alkyl component of the arylalkyl or alkylaryl unit.

The term "halogen" shall include fluorine, chlorine, iodine and bromine.

The term "oxy" shall mean an oxygen (0) atom. The term "oxo" refers to a bivalent oxygen atom (=0). The term "thio" shall mean a sulfur (S) atom.

The site at which bone growth stimulation is desired is meant both the area adjacent to a section of bone or group of bones in need of treatment in a human or other organism in need thereof or a region inside the bone, including the site of a fracture or opening which occurs naturally or is intentionally made in the bone or group of bones.

The term "broken bone" means all types of broken bones such as green stick fractures, compound fractures, lateral fractures, pathologic fractures resulting from invasive tumors, compression fractures and fractures that require surgical procedures for realignment of bones.

The term "bisphosphonate delivery agent" as recited herein means any known bisphosphonate that effectively targets bone and is capable of reacting with a prostaglandin as recited herein. The bisphosphonate delivery agents include all commercially known bisphosphonates used in the treatment of osteoporosis and further includes those specifically recited in this disclosure. The above term also includes those bisphosphonates that target bone and are safe and effective whether or not the bisphosphonate is useful in the treatment of osteoporosis.

In the schemes and examples below, various reagent symbols have the following meanings:
BOC(Boc): t-butyloxycarbonyl.
THP: tetrahydropyran
Pd-C: Palladium on activated carbon catalyst.
DMF: Dimethylformamide.
DMSO: Dimethylsulfoxide.
DCC: 1,3-Dicyclohexylimidazole
CBZ(CBz): Carbobenzyloxy or benzyloxycarbonyl.
$CH_2Cl_2$: Methylene chloride.
$CHCl_3$: chlorform.
$CH_3CN$: acetonitrile
EtOH: ethanol.
CDI: Carbonyldiimidazole
MeOH: methanol.
EtOAc: ethylacetate.
HOAc: acetic acid.
EDC: 1-(3-Dimethylaminopropyl)-3-ethylcarbo-diimide
LDA: Lithium diisopropylamide
THF: tetrahydrofuran The compounds of the present invention can be administered in such oral forms as tablets, capsules (each of which includes sustained release or timed release formulations), pills, powders, granules, elixers, tinctures, suspensions, syrups, and emulsions. Likewise, they may be administered in intravenous (bolus or infusion), intraperitoneal, subcutaneous, or intramusculsar form, all using forms well known to those of ordinary skill in the pharmaceutical arts. An effective but nontoxic amount of the compound desired can be employed as an anti-osteoporosis agent or as a fracture healing agent.

Compounds of the invention may be administered to patients where prevention of osteoporosis or other bone related disorder is desired.

The dosage regimen utilizing the compounds of the present invention is selected in accordance with a variety of factors including type, species, age, weight, sex and medical condition of the patient; the severity of the condition to be treated; the route of adminstration; the renal and hepatic function of the patient; and the particular compound or salt thereof employed. An ordinarilly skilled physician or veterinarian can readily determine and prescribe the effective amount of the drag required to prevent, counter, or arrest the progress of the condition.

In the methods of the present invention, the compounds herein described in detail can form the active ingredient, and are typically administered in admixture with suitable pharmaceutical diluents, excipients or carders (collectively referred to herein as "carrier" materials) suitably selected with respect to the intended form of administration, that is, oral tablets, capsules, elixers, syrups and the like, and consistent with convention pharmaceutical practices.

For instance, for oral administration in the form of a tablet or capsule, the active drag component can be combined with an oral, nontoxic, pharmaceutically acceptable, inert carder such as lactose, starch, sucrose, glucose, methyl cellulose, magnesium sterate, dicalcium phosphate, calcium sulfate, mannitol, sorbitol and the like; for oral administration in liquid form, the oral drag components can be combined with any oral, non-toxic, pharmaceutically acceptable inert carder such as ethanol, glycerol, water and the like. Moreover, when desired or necessary, suitable binders, lubricants, disintegrating agents, electrolytes, and coloring agents can also be incorporated into the mixture. The present composition may be administered in the form of tablets, caplets, gelcaps, capsules, elixirs, syrups, or suspensions.

For oral administration, the active ingredients may be admixed with a pharmaceutically acceptable diluent such as lactose, sucrose, cellulose, dicalcium phosphate, calcium sulfate, mannitol, and, in a liquid composition, ethyl alcohol. Acceptable emulsifying or suspending agents such as PVP, gelatin, natural sugars, corn sweeteners, natural and synthetic gums such as acacia, sodium alginate, guar gum, agar, bentonite, carboxymethylcellulose sodium, polyethylene glycol and waxes, may also be admixed with the active components. Where necessary, lubricants such as magnesium stearic acid talc or magnesium stearate, and disintegrators or superdisintegrators such as starch, sodium starch glycolate or cross-linked PVP may also be included. Electrolytes such as dicalcium phosphate, sodium benzoate, sodium acetate and sodium chloride may also be used. Disintegrators also include, without limitation, starch methyl cellulose, agar, bentonite, xanthan gum and the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of the present invention may also be coupled with soluble polymers as targetable drug carriers. Such polymers can include poly-vinlypyrrolidone, pyran copolymer, polyhydroxypropyl-methacrylamide-phenol, polyhydroxyethylaspartamide-phenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

The compounds of the present invention can also be co-administered with suitable anti-osteoporosis drags to achieve synergystic effects in the treatment of various pathologies. They may also be combined with known bisphosphonates or other suitable compounds which are used to treat osteoporosis, bone-related disorders, or bone fractures.

The novel compounds of the present invention were prepared according to the procedure of the schemes and examples described in this specification, using appropriate materials and are further exemplified by the following specific examples. The most preferred compounds of the invention are any or all of those specifically set forth in these examples and schemes. These compounds are not, however, to be construed as forming the only genus that is considered as the invention, and any combination of the compounds or their moieties may itself form a genus. The following examples further illustrate details for the preparation of the compounds of the present invention. Those skilled in the art will readily understand that known variations of the conditions and processes of the following preparative procedures can be used to prepare these compounds. All temperatures are degrees Celcius unless otherwise noted.

EXAMPLES

Example 1

Synthesis of $PGE_2$-ABP Sodium Compound 1,3-Dicyclohexylcarbodiimide (3.6 mg) was added to a stirred solution of $PGE_2$ (I) (3.1 mg) and N-hyroxysuccinimide (3.0 mg) in dry acetonitrile (200 μL) and stirred at room temperature (25° C.) until thin layer chromatography indicated that the reaction was complete. The solvent is removed under an inert atmosphere (nitrogen) and the residue was dissolved in methylene chloride and applied to a small column of silica gel in a pasteur pipette. The pipette was then eluted with ethyl acetate (EtOAc) to afford the hydroxysuccinimide ester (IIa) and a small quantity of dicyclohexylurea. ($CDCl_3$) 5.45–5.7 (2H, m, H-13, 14), 5.37 (2H, m, s H-5,6), 3.95–4.15 (2H, m, H-11,15), 2.85 (4H, s, $O=C(CH_2)_2/CO$). A solution of this ester in 1,4-dioxane was added to a stirred solution of ABP disodium salt (2.4 mg) in water (150 μL) and 1.0 molar (M) aqueous NaOH (10 μL). After 10 minutes or so the pH of the reaction mixture was adjusted to approximately 9 with 1.0M aqueous NaOH, and then 1 hr later the pH was adjusted to 7 with 0.1M aqueous HCl. The solution is filtered and the filtrate was concentrated to dryness. The residue was then dissolved in water and applied to a Varian Bond Elute $C_{18}$ pak which was eluted with water. When the product began to elute, the solvent system on the $C_{18}$ column was changed to acetonitrile/water (50:50). Evaporation of fractions containing the product afforded the target amide (III) (3.7 mg). ($D_2O$) (2H, m, H-5,6), 5.1–5.4 (2H, m, H-13,14), 3.9–4.1 (2H, m, H-11,15), 3.0 (2H, t, $HN-CH_2$).

Example 2

The identical procedure as described in Example 1 was followed with tritiated $PGE_2$ and $^{14}C$ labeled ABP monosodium salt to produce a compound with the following structure:

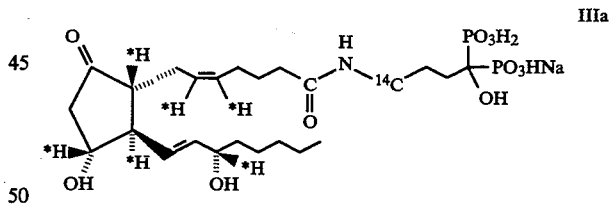

IIIa

This compound was then used in the following in vitro and in vivo experiments to exemplify the release of the $PGE_2$ moiety from bone cells after administration of the claimed compound and to exemplify and demonstrate that the claimed compound is attached in vivo to bone.

Example 3

Synthesis of a $PGE_2$-Dithio Compound as depticted in Scheme 13

Dicyclohexylcarbodiimide (0.2 g) was added to a stirred solution of N-(4-carboxybutyl)maleimide (0.12 g) [m.p. 87–89° C. prepared in the same way as the procedure in Coleman et al, J. Org. Chem., 1959, 24, 135] in dichloromethane (10 ml) containing N-hydroxysuccinimide (0.38 g). After two hours, the reaction mixture was poured onto a silica gel column which was eluted with ethyl acetate affording the active ester (1)

(0.086 g). $^1$H NMR [(CD$_3$)$_2$CO]δ6.85(2H, s), 3.50(2H,t), 2.87(4H,s), 2.72(2H,t ), 1.98(2H,dt).

A solution of the active ester (1) (12 mg) in 1,4-dioxane (200 μl) was added to a stirred solution of bisphosphonate (ABP) (7 ng) in water (400 μl) and 1 N sodium hydroxide (25 μl). After 15 minutes the solution was adjusted to pH 7 with 0.1 N HCl and then lyophilized. The resulting powder was dissolved in water and eluted through two Varian 6 ml C$_{18}$ "bond elute" cartridges with water, collecting the first 4 nl from each cartridge. This solution was lyophilized and the resulting colorless powder contained the maleimide derivative (3) as well as N-hydroxysuccinamide and, perhaps, some unreacted ABP. $^1$H NMR (D$_2$O)δ6.72(2H,s), 3.40(2H,t), 3.01(2H,t), 2.13(2H,t), 1.9–1.6(6H,m).

A solution of PGE$_2$ (4) (5 mg) in CH$_2$Cl$_2$ (500 μl) was stirred under nitrogen and treated with 1,3-propanedithiol (14 μl) and dicyclohexylcarbodiimide (8 ng). The reaction was followed by thin layer chromatography (t.l.c.) and when complete (~4 hours) the reaction mixture was poured onto a small silica gel column in a pasteur pipette. Elution with deoxygenated ethyl acetate afforded the thiolester (5). This was immediately dissolved in methanol (500 μl) and added to a solution of (4) in aqueous methanol (1 ml, 1:1 v/v). The solution was allowed to stand for 15 minutes, then most of the methanol was evaporated and the residual aqueous solution was freeze-dried. The crude product was dissolved in water and absorbed onto a Varian 6 ml C-18 bond elute cartridge. This was eluted with water (9 ml), 30% MeOH/H$_2$O (6 ml), then 60% MeON/H$_2$O (6 ml). The first 3 ml of the 60% MeOH fraction contained all the product (6) obtained as a white powder (4.6 mg) after lyophilization. m.p. >260° C. (dec).

$^{13}$C NMR (D$_2$O)δ(ppm) 215.7(C=O), 198.2 (C—S), 176.0, 176.1,172.2 (C—N), 133.8, 129.6, 127.7, 124.5 (HC=), 71.1(t, Jclp=134 Hz, C-p), 70.2, 68.4(CH—O), 51.7, 50.6, 37.0(CH), 43.2, 40.6, 37.4, 35.9, 34.0, 33.4, 30.3, 28.9, 28.4, 27.4, 26.1, 24.8, 23.6, 22.5, 20.8, 20.6, 19.9(CH$_2$), 11.3(CH$_3$).

Example 4

The identical procedure as described in Example 3 was followed with tritiated PGE$_2$ and $^{14}$C labeled ABP monosodium salt to produce a compound with the following structure:

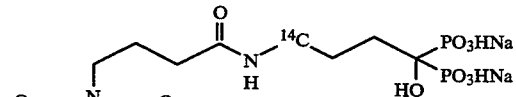
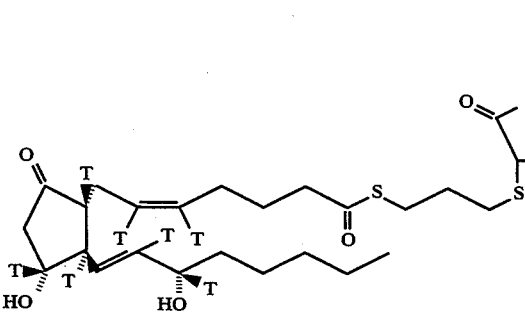

The above compound was used in the same biological experiments as the compound IIIa as a delivery agent of labeled prostaglandin.

Biological Experiments

Example 5

Binding of (IIIa) to bone powder

1 μl of $^3$H-PGE$_2$/$^{14}$C-ABP (IIIa) (21.64 μCi of $^{14}$C and 19.05 μCi of $^3$H) was placed in 1 ml 100% fetal bovine serum to yield a final concentration of 3.5 μM. 200 ml of this solution was incubated with 10 mg bone powder for 1, 2, 3 and 5 mins with vigorous shaking. The mixture was centrifuged (20 sec), 125 μl aliquot was taken from each sample and counted in 10 ml Atomlight in an LKB liquid scintillation counter. 125 μl of the radioactive sample was also counted at 0 time. The uptake of radioactivity into the bone powder was calculated by subtracting the dpms in the medium counted at the times indicated above from dpms at 0 time and this number was divided by the dpms at 0 time. The data demonstrated that about 76% of the $^{14}$C-moiety and 53% of the $^3$H-moiety were taken up by bone particles within 1 min. In a separate experiment, we found that 77% $^3$H-ABP was taken up by bone in 1 min.

Example 6

The $^3$H moiety associated with the PGE$_2$ component of the molecule and its release into the medium surrounding the collected bone particles was measured over a period of hours to days. The data suggested that 5% release occurred per day.

Dissociation of $^3$H-PGE$_2$/$^{14}$C-ABP (IIIa) from human bone powder

Dissociation of $^3$H-PGE$_2$/$^{14}$C-ABP from human bone powder in fetal bovine serum at 37° C. was measured by incubating 10 mg of human bone powder with 1 μl $^3$H-PGE$_2$/$^{14}$C-ABP in 1 ml for 5 mins. The mixture was centrifuged (20 sec), 100 μl aliquot was taken and counted in Atomlight in an LKB liquid scintillation counter. The rest of the 900 μl solution was withdrawn, the bone powder was washed once with 1 ml phosphate buffered saline, 1 ml fresh fetal bovine serum was added and incubated with the bone powder for. 15, 24, 39, 48, 59, 79 and 103 hours in a shaking bath at 37° C. 100 μl aliquots were withdrawn at these times and counted in 10 mls Atomlight in an LKB liquid scintillation counter. The release of radioactivity from the human bone powder into the medium was calculated as follows: dpms from 100 μl of the $^3$H-PGE$_2$/$^{14}$C-ABP at 5 mins were subtracted from dpms at 0 time. The resulting dpms reflect radioactivity taken up by bone powder. The dpms obtained by counting 100 μl aliquots at each time point were then divided by the dpms taken up by bone. 13% of the $^3$H-moiety was released into the medium at 15 hrs and by 103 hours 32.9% of the radioactivity was released into the medium. About 5% of the $^3$H-moiety was released per day whereas the dpms of $^{14}$C-moiety in the medium were not significantly changed during this time frame.

Example 7

Uptake of ³H-ABP or ³H-PGE₂/¹⁴C-ABP (IIIa) in rat tibia and femora

Both compounds were administered intravenously via the tail vein to Sprague-Dawley female rats as a single dose of 28 nmoles of radiolabeled compound, equivalent to 0.2 μCi/animal. ³H-ABP, which was administered to nine rats, is correspondent to 0.1 mg/kg and ³H-PGE₂/¹⁴C-ABP (IIIa), which was administered to seven rats, is correspondent to 0.24 mg/kg. After 1, 14 or 28 days, animals were sacrificed by $CO_2$ and the tibia and femora were dissected weighed and then stored at −20° C. The amount of radioactivity incorporated into the bone was determined by incineration in a Packard combuster after first air drying the bone for three days at ambient temperature. The percent of the compound retained in bone at each time point was calculated on the basis of the radioactivity, converted to nmoles/gm bone on the assumption that the skeleton represents 8 % of the body weight. The skeletal retention was expressed as percent administered dose. FIG. 1 shows the relative percentage of compound IIIa retained in rat tibiae and femora versus the bisphosphonate ³H-alendronate (4-amino-1-hydroxybutylidene bisphosphonic acid disodium salt).

Example 8

Figure 2:
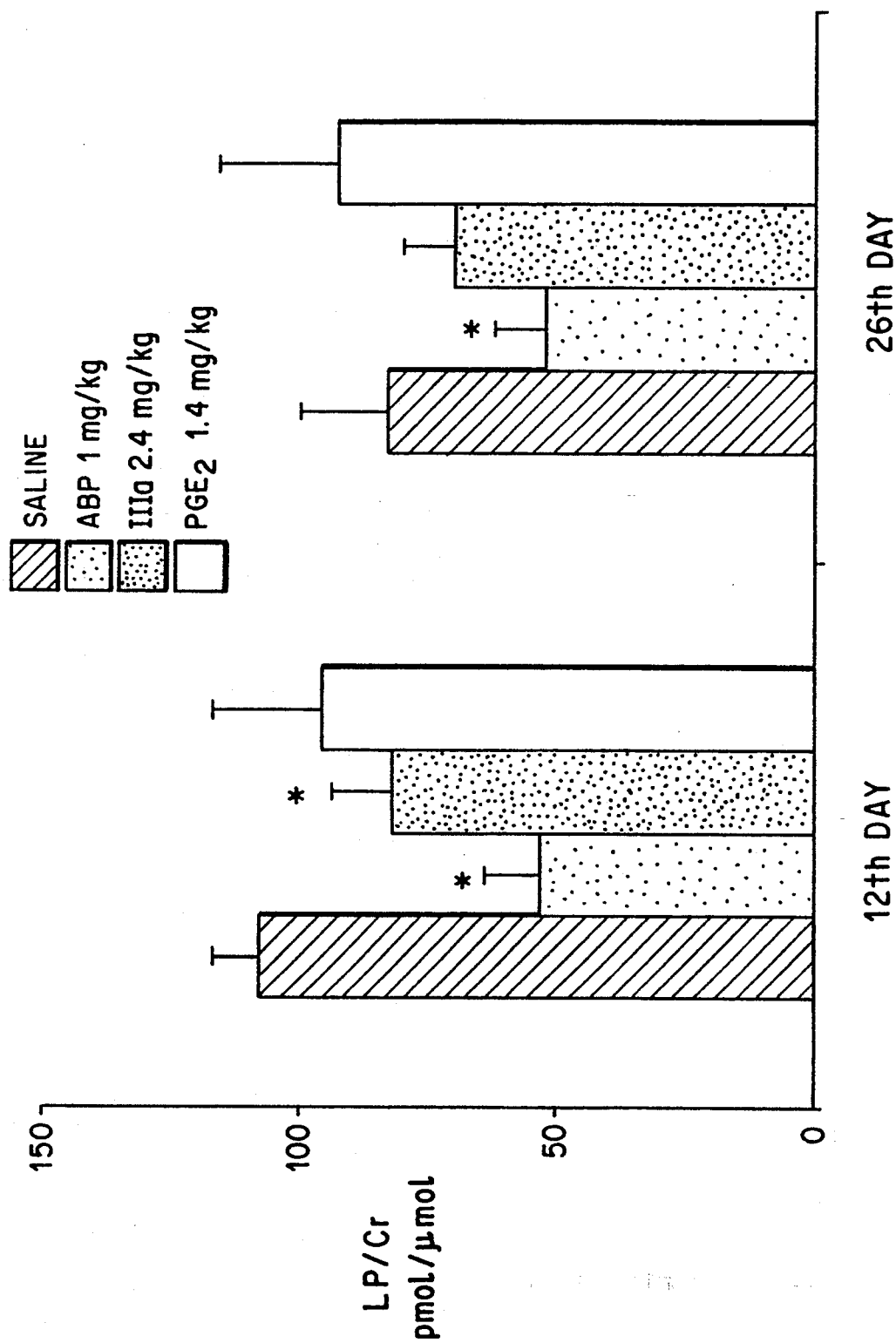
FIG. 2 shows the effect of IIIa on bone resorption estimated by urinary lysylpyridinoline in the rat versus various other compounds-alendronate, saline and PGE₂. Lysylpyridinoline concentration is a measure of the breakdown of bone collagen. The results showed that at 12 and 26 days, alendronate treated animals had lower levels of LPs (inhibition of bone resorption) compared to vehicle treated animals while IIIa treated animals at 12 days had significantly lower levels of LP; at 26 days this difference was not significant.

Effect of PGE₂/ABP (IIIa) on bone resorption estimated by urinary excretion of lysypyridinoline in the rat 4 week old Sprague-Dawley female rats were injected intravenously via the tail vein with equimolar weekly doses of ABP (1 mg/kg, n=5), PGE₂/ABP (2.4 mg/kg, n=5), PGE₂ (1.4 mg/kg, n=5), or saline (n=4) each. Filtered urine was collected after 12 and 26 days by housing individual rats in metabolic cages and providing them with food and water ad libitum. The overnight collections of urine were centrifuged at 1000×g for 10 minutes to remove any particles and the supernatant fluid was stored at −80° C. until analysis. Lysylpyridinoline (LP) was extracted from duplicate 1 ml aliquots by acid hydrolysis and subsequent low pressure CF-1 chromatography according to the method of Beardsworth et al. (1990). LP was further resolved by high pressure liquid chromatography according to the method of Uebelhart et al. (1990) and quantitated by comparison with an external standard. Urinary creatinine was measured using the picric acid colorimetric assay (Pharmacia Diagnostics Inc., Fairfield, N.J.). Final results were expressed as pmoles LP per μmole creatinine. The results as depicted in FIG. 2 showed that animals treated with compound IIIa had significantly lower levels of LP after a 12 day period compared to vehicle alone. References which describe the procedures utilized in the above examples include: Beardsworth, L. J., Eyre, D. R., and Dickson I. R. 1990 Journal of Bone and Mineral Research 5 (7):671-676 and Uebelhart, D, Gineyts, E, Chapuy, M. C., and Delmas, P. D. 1990 Bone and Mineral 8:87-96.

Example 9

ABP, PGE₂/ABP, and PGE₂ effects on bone loss due to limb immobilization in the rat Male Sprague-Dawley rats weighing 270 grams (10-12 wks) were injected subcutaneously on two consecutive days prior to unilateral sciatic neurectomy induced hindlimb immobilization with the following doses: Vehicle (0.0 mg/kg), ABP (0.5mg/kg), PGE₂/ABP (1.2 mg/kg), PGE₂ (0.7 mg/kg). Ten days post-neurectomy femora were removed at necropsy, dissected from the musculature, and placed in crucibles for incineration at 700° C. for twenty-four hours. Following incineration, the femoral ash content was weighed to the nearest 0.1 mg and the femoral ash weight differences between the control and immobilized hindlimb were calculated. Data represent mean ±SEM (n=6). The results showed that in this particular experiment there was no statistical difference between PGE₂, the labeled compound claimed within the scope of the instant invention, and an inert vehicle in preventing bone loss which accompanies limb immobilization in the rat. ABP alone used as a positive control was effective.

We claim:

1. A compound of the formula:

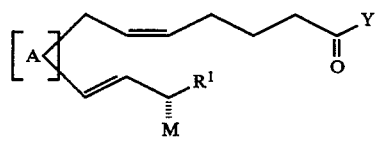

and the pharmaceutically acceptable salts thereof wherein: [A] is a dioxygenated cyclopentane moiety of the formula:

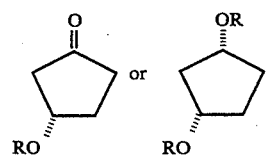

wherein
R is:
  H,
  THP, or
  Si(CH₃)₂tBu:
R¹ is:
  H, or
  C₁₋₁₀ alkyl;
M is:
  OH,
  OC₁₋₆ alkyl,

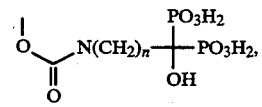

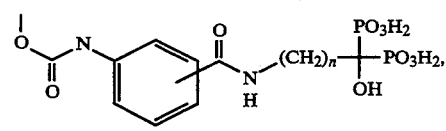

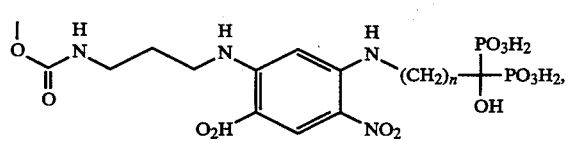

-continued

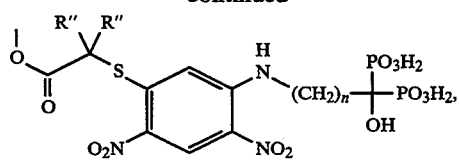

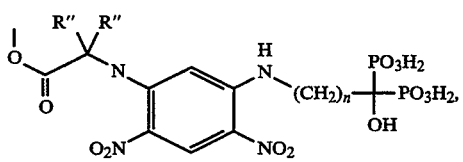

wherein R" is H, C$_{1-10}$ alkyl, aryl, or benzyl;

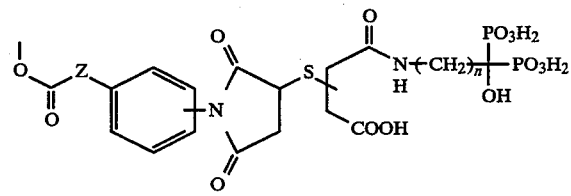

wherein Z is NH, C(R$^1$)$_2$, or absent; or

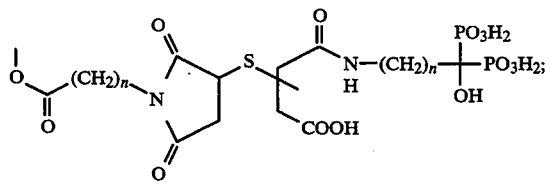

Y is:
OR' wherein R' is C$_{1-6}$ alkyl;

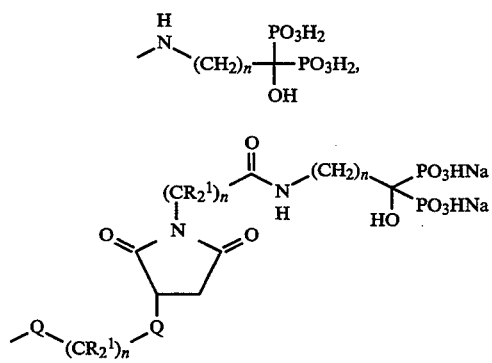

wherein Q is NR$^1$, O, or S;

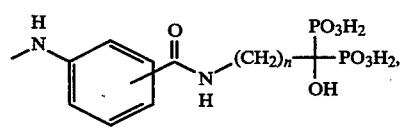

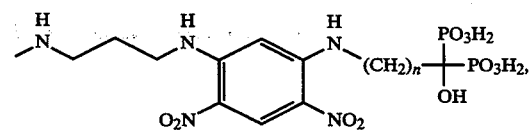

-continued

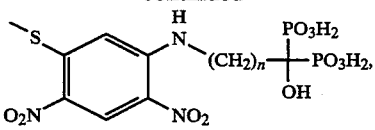

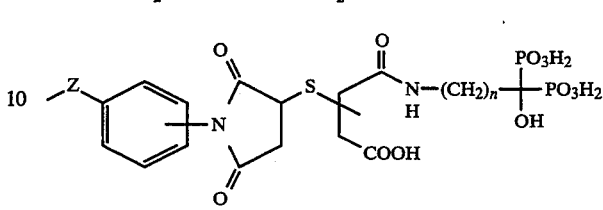

wherein Z is NH, C(R$^1$)2 or absent; or

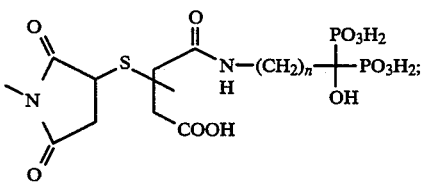

and n is an integer from 0–10 provided that when M is OH, or OC$_{1-6}$alkyl Y is not OR$^1$.

2. The compound according to claim 1 of the formula:

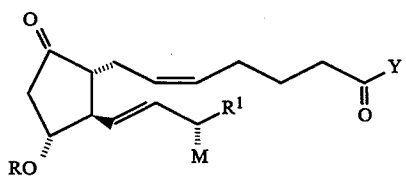

wherein
R is:
 H,
 THP, or
 Si(CH$_3$)$_2$tBu;
R$^1$ is:
 H, or
 C$_{1-10}$ alkyl;
M is:
 OH,
 OC$_{1-6}$ alkyl

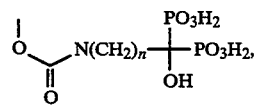

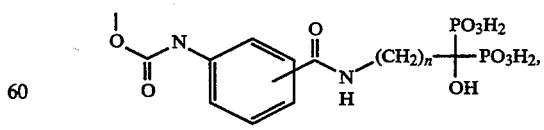

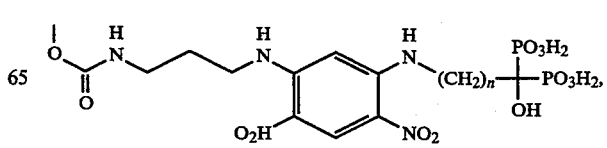

-continued
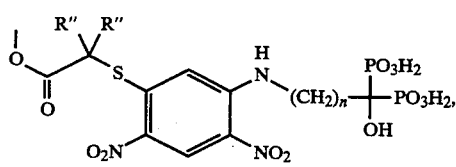
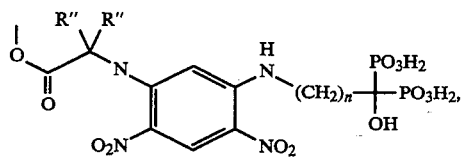
wherein R″ is H, C$_{1-10}$ alkyl, aryl, or benzyl;
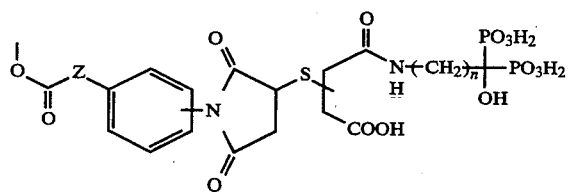
wherein Z is NH, C(R$^1$)$_2$, or absent; or
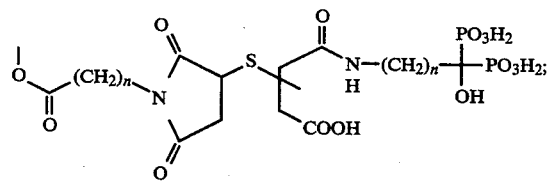
Y is:
OR′ wherein R′ is C$_{1-6}$ alkyl;
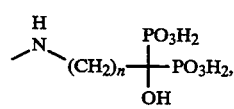
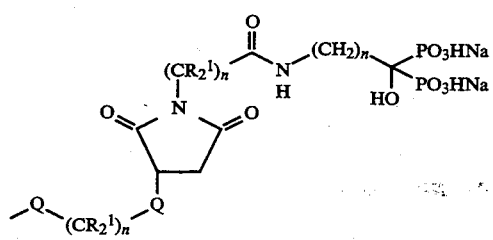
wherein Q is NR$^1$, O, or S;
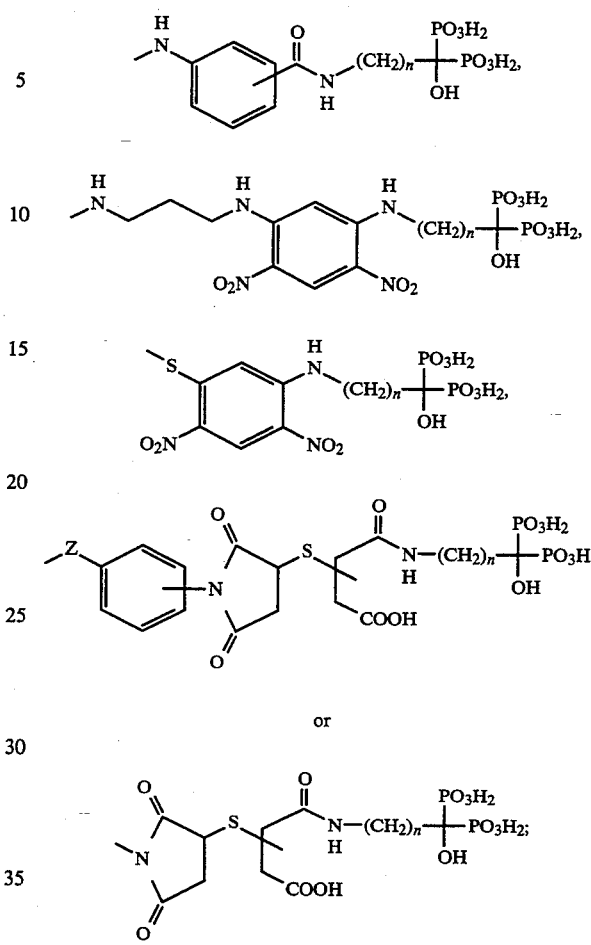
and n is an integer from 0–10.
3. The compound according to claim 2 of the formula:
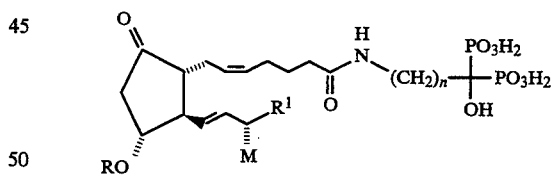
wherein
R is:
H,
THP, or
Si(CH$_3$)$_2$tBu;
R$^1$ is:
C$_{1-10}$ alkyl;
M is:
OH, or
OC$_{1-6}$ alkyl;
and n is an integer from 0–10.
4. The compound according to claim 2 of the formula:

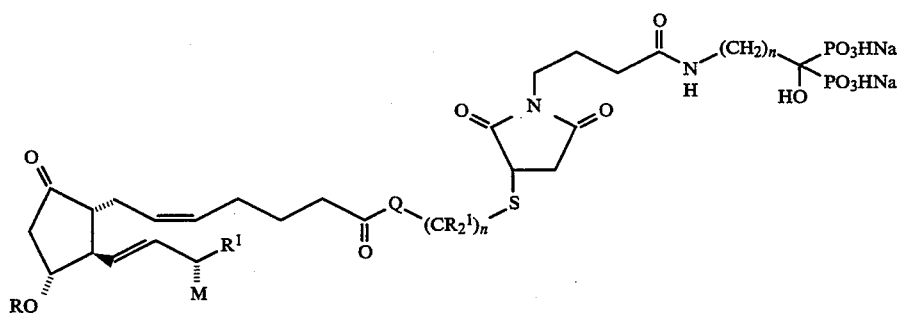
wherein
R is:
  H,
  THP, or
  Si(CH$_3$)$_2$tBu;
R$^1$ is:
  H, or
  C$_{1-10}$ alkyl;
M is:
  OH, or
  OC$_{1-6}$ alkyl;
Q is O, NR$^1$, or S;
and n is an integer from 0–10.
5. The compound according to claim 2 of the formula:
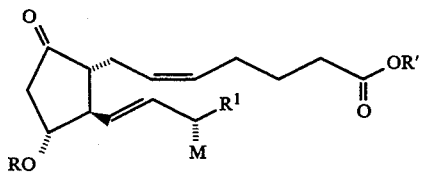
wherein
R is
  H,
  THP, or
  Si(CH$_3$)$_2$tBu;
R' is:
  C$_{1-6}$ alkyl;
R$^1$ is:
  H, or
  C$_{1-10}$ alkyl;
M is:
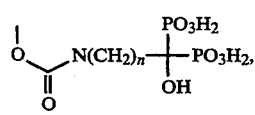
-continued
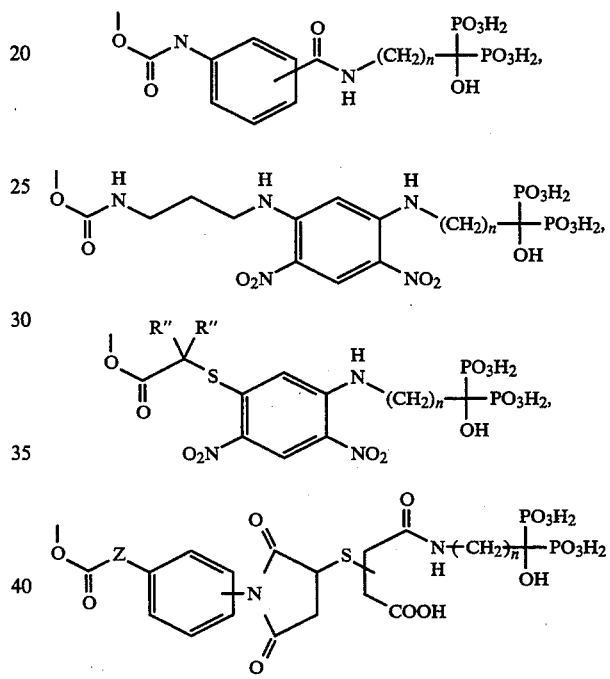
wherein Z is NH, C(R$^1$)$_2$, or absent; or
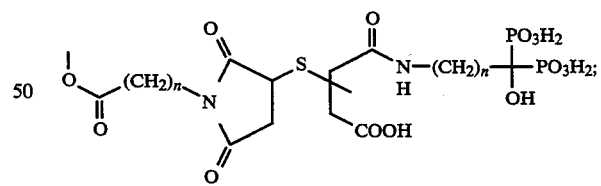
and n is an integer from 0–10.
6. The compound according to claim 2 of the formula:
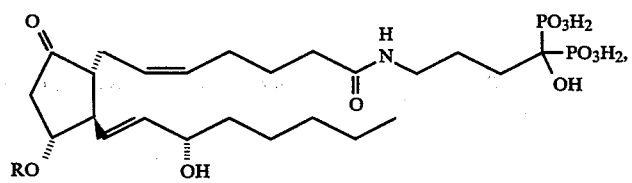

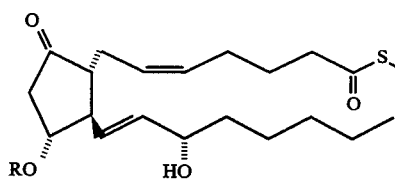

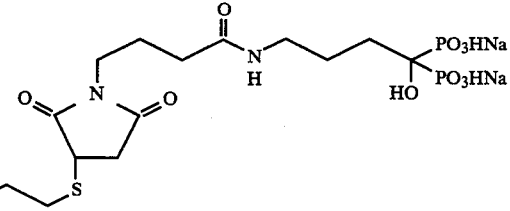
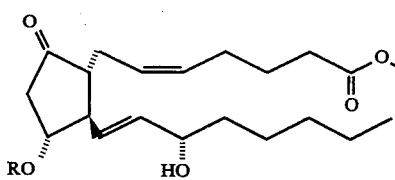

and the pharmaceutically acceptable salts thereof.

7. The compound according to claim 5 of the formula:

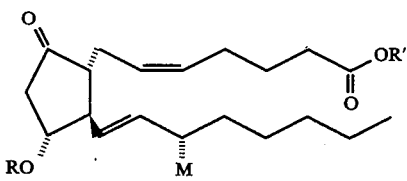

wherein
R is:
 H,
 THP, or
 Si(CH$_3$)$_2$tBu;
R' is:
 C$_{1-6}$ alkyl;
M is:

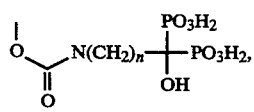

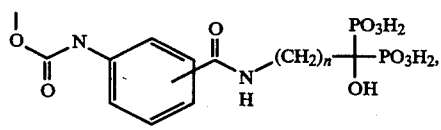

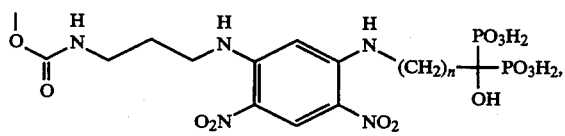

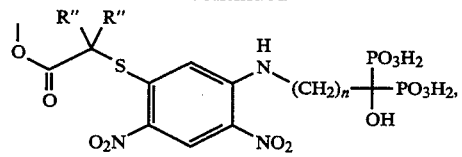

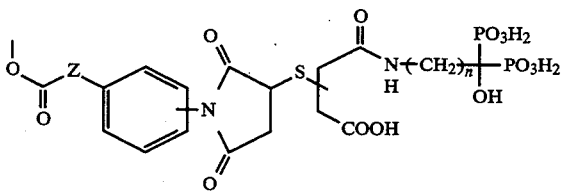

wherein Z is NH, C(R$^1$)$_2$, or absent; or

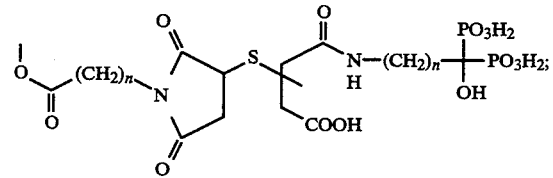

and n is an integer from 0–10.

8. A method of treating or preventing osteoporosis by administering a pharmaceutically effective amount of the compound according to claim 1.

9. A method of increasing the bone fracture healing rate in a mammal exhibiting a bone fracture by systemically administering a pharmaceutically effective amount of the compound according to claim 1.

10. A method for enhancing the rate of successful bone grafts comprising administering to a mammal in need thereof a pharmaceutically effective amount of the compound according to claim 1.

11. A pharmaceutical composition comprising the compound as claimed in claim 1 and a pharmaceutically acceptable carrier.

12. A pharmaceutical composition according to claim 11 for the treatment and prevention of osteoporosis.

13. A pharmaceutical composition according to claim 11 for enhancing bone formation rates in patients in need of treatment thereof.

* * * * *